United States Patent
Deng et al.

(10) Patent No.: US 12,257,266 B2
(45) Date of Patent: Mar. 25, 2025

(54) STEM CELL-DERIVED EXOSOMES FOR THE TREATMENT OF CORNEAL SCARRING

(71) Applicants: The Regents of the University of California, Oakland, CA (US); University of Pittsburgh—Of the Commonwealth System of Higher Education, Pittsburgh, CA (US)

(72) Inventors: Sophie Xiaohui Deng, Los Angeles, CA (US); James L. Funderburgh, Pittsburgh, PA (US)

(73) Assignees: THE REGENTS OF THE UNIVERSITY OF CALIFORNIA, Oakland, CA (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 1211 days.

(21) Appl. No.: 16/977,015

(22) PCT Filed: Mar. 4, 2019

(86) PCT No.: PCT/US2019/020516
§ 371 (c)(1),
(2) Date: Aug. 31, 2020

(87) PCT Pub. No.: WO2019/169380
PCT Pub. Date: Sep. 6, 2019

(65) Prior Publication Data
US 2021/0000858 A1 Jan. 7, 2021

Related U.S. Application Data

(60) Provisional application No. 62/638,045, filed on Mar. 2, 2018.

(51) Int. Cl.
| | | |
|---|---|---|
| A61K 31/7105 | (2006.01) | |
| A61K 9/00 | (2006.01) | |
| C12N 15/113 | (2010.01) | |

(52) U.S. Cl.
CPC ........ *A61K 31/7105* (2013.01); *A61K 9/0019* (2013.01); *A61K 9/0048* (2013.01); *C12N 15/113* (2013.01); *C12N 2310/141* (2013.01); *C12N 2320/32* (2013.01)

(58) Field of Classification Search
None
See application file for complete search history.

(56) References Cited

U.S. PATENT DOCUMENTS

| | | |
|---|---|---|
| 2011/0263680 A1 | 10/2011 | Khvorova et al. |
| 2013/0143314 A1* | 6/2013 | Shiels ............... G01N 33/5061 435/320.1 |
| 2014/0234263 A1* | 8/2014 | Shiels ...................... A61P 3/10 424/93.7 |
| 2015/0267196 A1 | 9/2015 | Alsberg et al. |
| 2016/0002597 A1 | 1/2016 | Sinden et al. |
| 2017/0152484 A1 | 6/2017 | Cho et al. |
| 2017/0209365 A1 | 7/2017 | Cho et al. |

FOREIGN PATENT DOCUMENTS

| | | | |
|---|---|---|---|
| WO | 2013079701 A3 | 7/2013 | |
| WO | 2015/002956 | 1/2015 | |
| WO | WO-2017160884 A1 * | 9/2017 | ............ A61K 35/12 |
| WO | 2017/188487 | 11/2017 | |

OTHER PUBLICATIONS

Grobe et al. "Characterization of vitamin C-induced cell sheets formed from primary and immortalized human corneal stromal cells for tissue engineering applications," Cells Tissues Organs, Feb. 1, 2013 (Feb. 1, 2013), vol. 197, No. 4, pp. 283-297.

Samaeekia et al. "Effect of Human Corneal Mesenchymal Stromal Cell-derived Exosomes on Corneal Epithelial Wound Healing," Invest Ophthalmol Vis Sci, Oct. 1, 2018 (Oct. 1, 2018), vol. 59, Iss. 12, pp. 5194-5200.

PCT International Search Report and Written Opinion dated Jul. 26, 2019 for PCT Application No. PCT/US2019/20516.

Shojaati et al. "Mesenchymal Stem Cells Reduce Corneal Fibrosis and Inflammation via Extracellular Vesicle-Mediated Delivery of miRNA," Stem Cells Translation Medicine, Jul. 10, 2019 (Jul. 10, 2019), pp. 1-10.

(Continued)

*Primary Examiner* — Christopher M Babic
*Assistant Examiner* — Kimberly A Aron
(74) *Attorney, Agent, or Firm* — GATES & COOPER LLP

(57) ABSTRACT

Corneal stromal scars are the leading cause of corneal blindness. The present invention relates to methods and compositions useful in therapies for this pathological condition. The invention provides corneal stromal stem cells and certain other stem cells and as well as exosome polynucleotides produced by such cells, and methods for making and using these cells and compositions. The invention is based upon the discovery that exosomes and their associate active components obtained from these cells comprise agents having the same capacity as corneal stromal stem cells to reduce scarring and prevent scar formation in patients having corneal damage.

7 Claims, 6 Drawing Sheets
Specification includes a Sequence Listing.

(56) References Cited

OTHER PUBLICATIONS

Bentwick I et al: "Identification of hundreds of conserved and nonconserved human microRNAs", Nature Genetics, Nature Publishing Group US, New York, vol. 37, No. 7, Jul. 1, 2005 (Jul. 1, 2005), pp. 766-770.
Han Kyu-Yeon et al: "Potential role of corneal epithelial cell-derived exosomes in corneal wound healing and neovascularization", Scientific Reports, [Online] vol. 7, No. 1, Feb. 1, 2017 (Feb. 1, 2017).
Extended European Search Report dated Mar. 21, 2022 for EP Application No. 19761388.8.

\* cited by examiner

| Gene | CSSC | CSSC/HEK | p value | PMID |
|---|---|---|---|---|
| hsa-miR-199a-3p | 10675 | 181 | 0.007 | 28408445 |
| hsa-miR-125b-5p | 9523 | 8 | 0.011 | 27388239 |
| hsa-miR-29a-3p | 8025 | 13 | 0.021 | 26056933 |
| hsa-miR-21-5p | 4850 | 15 | 0.020 | 29843043 |
| hsa-miR-222-3p | 4826 | 6 | 0.032 | 25863248 |
| hsa-let-7b-5p | 3053 | 39 | 0.000 | 24088962 |
| hsa-miR-574-3p | 2447 | 34 | 0.020 | |
| hsa-miR-146a-5p | 1887 | 77 | 0.000 | 25999712 |
| hsa-miR-381-5p | 1676 | 85 | 0.003 | |
| hsa-miR-141-3p | 1498 | 55 | 0.000 | 22622653 |
| hsa-miR-138-5p | 1421 | 96 | 0.012 | 25953925 |
| hsa-miR-654-5p | 1247 | 127 | 0.000 | |
| hsa-miR-146b-5p | 1204 | 61 | 0.000 | 28714020 |
| hsa-miR-409-3p | 1045 | 142 | 0.000 | |
| hsa-miR-125a-3p | 1024 | 35 | 0.009 | 22747700 |
| hsa-miR-590-3p | 991 | 134 | 0.001 | 28408445 |
| hsa-miR-92b-3p | 983 | 13 | 0.000 | |
| hsa-miR-381-3p | 948 | 64 | 0.002 | |
| hsa-miR-206 | 947 | 64 | 0.000 | 25953925 |
| hsa-miR-889-3p | 926 | 54 | 0.001 | |
| hsa-miR-485-3p | 918 | 42 | 0.000 | |
| hsa-miR-539-3p | 914 | 53 | 0.000 | |
| hsa-miR-200c-3p | 870 | 71 | 0.002 | 22622653 |
| hsa-miR-208a-3p | 761 | 44 | 0.002 | 25953925 |
| hsa-miR-654-3p | 756 | 77 | 0.000 | |
| hsa-miR-133a-3p | 693 | 47 | 0.001 | 25953925 |
| hsa-miR-431-5p | 623 | 127 | 0.005 | |
| hsa-miR-1306-3p | 611 | 50 | 0.001 | |
| hsa-miR-409-5p | 603 | 82 | 0.004 | |
| hsa-miR-493-3p | 528 | 54 | 0.000 | |
| hsa-miR-134-3p | 523 | 43 | 0.002 | 27321552 |

FIG. 6

SEQUENCE LISTING

<160> NUMBER OF SEQ ID NOS: 107

<210> SEQ ID NO 1
<211> LENGTH: 22
<212> TYPE: RNA
<213> ORGANISM: Homo sapiens

<400> SEQUENCE: 1
aacccguaga uccgaacuug ug                                              22

<210> SEQ ID NO 2
<211> LENGTH: 23
<212> TYPE: RNA
<213> ORGANISM: Homo sapiens

<400> SEQUENCE: 2
agcagcauug uacagggcua uca                                             23

<210> SEQ ID NO 3
<211> LENGTH: 21
<212> TYPE: RNA
<213> ORGANISM: Homo sapiens

<400> SEQUENCE: 3
uaggacacau ggucuacuuc u                                               21

<210> SEQ ID NO 4
<211> LENGTH: 21
<212> TYPE: RNA
<213> ORGANISM: Homo sapiens

<400> SEQUENCE: 4
agugaaugau ggguucugac c                                               21

<210> SEQ ID NO 5
<211> LENGTH: 19
<212> TYPE: RNA
<213> ORGANISM: Homo sapiens

<400> SEQUENCE: 5
auggauaagg cuuuggcuu                                                  19

<210> SEQ ID NO 6
<211> LENGTH: 21
<212> TYPE: RNA
<213> ORGANISM: Homo sapiens

<400> SEQUENCE: 6
ugcaggacca agaugagccc u                                               21

<210> SEQ ID NO 7
<211> LENGTH: 19
<212> TYPE: RNA
<213> ORGANISM: Homo sapiens

```
<400> SEQUENCE: 7
uggauuuuug gaucaggga                                          19

<210> SEQ ID NO 8
<211> LENGTH: 21
<212> TYPE: RNA
<213> ORGANISM: Homo sapiens

<400> SEQUENCE: 8
uuaggccgca gaucugggug a                                       21

<210> SEQ ID NO 9
<211> LENGTH: 17
<212> TYPE: RNA
<213> ORGANISM: Homo sapiens

<400> SEQUENCE: 9
uucaaguaau ucaggug                                            17

<210> SEQ ID NO 10
<211> LENGTH: 24
<212> TYPE: RNA
<213> ORGANISM: Homo sapiens

<400> SEQUENCE: 10
uuaaugcuaa ucgugauagg gguu                                    24

<210> SEQ ID NO 11
<211> LENGTH: 22
<212> TYPE: RNA
<213> ORGANISM: Homo sapiens

<400> SEQUENCE: 11
uagguaguuu cauguuguug gg                                      22

<210> SEQ ID NO 12
<211> LENGTH: 21
<212> TYPE: RNA
<213> ORGANISM: Homo sapiens

<400> SEQUENCE: 12
uaacagucuc cagucacggc c                                       21

<210> SEQ ID NO 13
<211> LENGTH: 23
<212> TYPE: RNA
<213> ORGANISM: Homo sapiens

<400> SEQUENCE: 13
cagugcaaug auauugucaa agc                                     23

<210> SEQ ID NO 14
<211> LENGTH: 18
<212> TYPE: RNA
<213> ORGANISM: Homo sapiens

<400> SEQUENCE: 14
aaagcugggu ugagaagg                                           18

<210> SEQ ID NO 15
<211> LENGTH: 22
<212> TYPE: RNA
```

```
<213> ORGANISM: Homo sapiens

<400> SEQUENCE: 15
aauugcacgg uauccaucug ua                                              22

<210> SEQ ID NO 16
<211> LENGTH: 22
<212> TYPE: RNA
<213> ORGANISM: Homo sapiens

<400> SEQUENCE: 16
gccugcuggg guggaaccug gu                                              22

<210> SEQ ID NO 17
<211> LENGTH: 21
<212> TYPE: RNA
<213> ORGANISM: Homo sapiens

<400> SEQUENCE: 17
aucauagagg aaaauccacg u                                               21

<210> SEQ ID NO 18
<211> LENGTH: 20
<212> TYPE: RNA
<213> ORGANISM: Homo sapiens

<400> SEQUENCE: 18
acuggacuug gagccagaag                                                 20

<210> SEQ ID NO 19
<211> LENGTH: 21
<212> TYPE: RNA
<213> ORGANISM: Homo sapiens

<400> SEQUENCE: 19
acuggacuug gugucagaug g                                               21

<210> SEQ ID NO 20
<211> LENGTH: 21
<212> TYPE: RNA
<213> ORGANISM: Homo sapiens

<400> SEQUENCE: 20
ugguagacua uggaacguag g                                               21

<210> SEQ ID NO 21
<211> LENGTH: 22
<212> TYPE: RNA
<213> ORGANISM: Homo sapiens

<400> SEQUENCE: 21
agcgagguug cccuuuguau au                                              22

<210> SEQ ID NO 22
<211> LENGTH: 21
<212> TYPE: RNA
<213> ORGANISM: Homo sapiens

<400> SEQUENCE: 22
uaguagaccg uauagcguac g                                               21

<210> SEQ ID NO 23
<211> LENGTH: 17
```

```
<212> TYPE: RNA
<213> ORGANISM: Homo sapiens

<400> SEQUENCE: 23
agggugugug uguuuuu                                                      17

<210> SEQ ID NO 24
<211> LENGTH: 17
<212> TYPE: RNA
<213> ORGANISM: Homo sapiens

<400> SEQUENCE: 24
auggagaagg cuucuga                                                      17

<210> SEQ ID NO 25
<211> LENGTH: 22
<212> TYPE: RNA
<213> ORGANISM: Homo sapiens

<400> SEQUENCE: 25
aaacaaacau ggugcacuuc uu                                                22

<210> SEQ ID NO 26
<211> LENGTH: 23
<212> TYPE: RNA
<213> ORGANISM: Homo sapiens

<400> SEQUENCE: 26
uuucaagcca gggggcguuu uuc                                               23

<210> SEQ ID NO 27
<211> LENGTH: 22
<212> TYPE: RNA
<213> ORGANISM: Homo sapiens

<400> SEQUENCE: 27
aaugcaccug ggcaaggauu ca                                                22

<210> SEQ ID NO 28
<211> LENGTH: 22
<212> TYPE: RNA
<213> ORGANISM: Homo sapiens

<400> SEQUENCE: 28
uucucaagag ggaggcaauc au                                                22

<210> SEQ ID NO 29
<211> LENGTH: 22
<212> TYPE: RNA
<213> ORGANISM: Homo sapiens

<400> SEQUENCE: 29
aaagugcuuc cuuuuagagg gu                                                22

<210> SEQ ID NO 30
<211> LENGTH: 22
<212> TYPE: RNA
<213> ORGANISM: Homo sapiens

<400> SEQUENCE: 30
aaacauucgc ggugcacuuc uu                                                22

<210> SEQ ID NO 31
```

```
<211> LENGTH: 20
<212> TYPE: RNA
<213> ORGANISM: Homo sapiens

<400> SEQUENCE: 31
aaaagugauu gcaguguuug                                                    20

<210> SEQ ID NO 32
<211> LENGTH: 22
<212> TYPE: RNA
<213> ORGANISM: Homo sapiens

<400> SEQUENCE: 32
aaaacuguaa uuacuuuugu ac                                                 22

<210> SEQ ID NO 33
<211> LENGTH: 22
<212> TYPE: RNA
<213> ORGANISM: Homo sapiens

<400> SEQUENCE: 33
gcuggugcaa aaguaauggc gg                                                 22

<210> SEQ ID NO 34
<211> LENGTH: 21
<212> TYPE: RNA
<213> ORGANISM: Homo sapiens

<400> SEQUENCE: 34
ugacaacuau ggaugagcuc u                                                  21

<210> SEQ ID NO 35
<211> LENGTH: 22
<212> TYPE: RNA
<213> ORGANISM: Homo sapiens

<400> SEQUENCE: 35
gaugagcuca uuguaauaug ag                                                 22

<210> SEQ ID NO 36
<211> LENGTH: 19
<212> TYPE: RNA
<213> ORGANISM: Homo sapiens

<400> SEQUENCE: 36
ugggcguauc uguaugcua                                                     19

<210> SEQ ID NO 37
<211> LENGTH: 21
<212> TYPE: RNA
<213> ORGANISM: Homo sapiens

<400> SEQUENCE: 37
uuuccauagg ugaugaguca c                                                  21

<210> SEQ ID NO 38
<211> LENGTH: 22
<212> TYPE: RNA
<213> ORGANISM: Homo sapiens

<400> SEQUENCE: 38
uacgucaucg uugucaucgu ca                                                 22
```

```
<210> SEQ ID NO 39
<211> LENGTH: 25
<212> TYPE: RNA
<213> ORGANISM: Homo sapiens

<400> SEQUENCE: 39
gcugggcagg gcuucugagc uccuu                                           25

<210> SEQ ID NO 40
<211> LENGTH: 20
<212> TYPE: RNA
<213> ORGANISM: Homo sapiens

<400> SEQUENCE: 40
aggaauguuc cuucuuugcc                                                 20

<210> SEQ ID NO 41
<211> LENGTH: 19
<212> TYPE: RNA
<213> ORGANISM: Homo sapiens

<400> SEQUENCE: 41
agcugucuga aaaugucuu                                                  19

<210> SEQ ID NO 42
<211> LENGTH: 22
<212> TYPE: RNA
<213> ORGANISM: Homo sapiens

<400> SEQUENCE: 42
aguauucugu accagggaag gu                                              22

<210> SEQ ID NO 43
<211> LENGTH: 19
<212> TYPE: RNA
<213> ORGANISM: Homo sapiens

<400> SEQUENCE: 43
aguguggcuu ucuuagagc                                                  19

<210> SEQ ID NO 44
<211> LENGTH: 23
<212> TYPE: RNA
<213> ORGANISM: Homo sapiens

<400> SEQUENCE: 44
ugggcagggg cuuauuguag gag                                             23

<210> SEQ ID NO 45
<211> LENGTH: 22
<212> TYPE: RNA
<213> ORGANISM: Homo sapiens

<400> SEQUENCE: 45
gcagcagggu gaaacugaca ca                                              22

<210> SEQ ID NO 46
<211> LENGTH: 22
<212> TYPE: RNA
<213> ORGANISM: Homo sapiens

<400> SEQUENCE: 46
ugagaccucu ggguucugag cu                                              22
```

```
<210> SEQ ID NO 47
<211> LENGTH: 21
<212> TYPE: RNA
<213> ORGANISM: Homo sapiens

<400> SEQUENCE: 47
uacucaaaaa gcugucaguc a                                              21

<210> SEQ ID NO 48
<211> LENGTH: 22
<212> TYPE: RNA
<213> ORGANISM: Homo sapiens

<400> SEQUENCE: 48
ugcaacuuac cugagucauu ga                                             22

<210> SEQ ID NO 49
<211> LENGTH: 21
<212> TYPE: RNA
<213> ORGANISM: Homo sapiens

<400> SEQUENCE: 49
ugucuugcag gccgucaugc a                                              21

<210> SEQ ID NO 50
<211> LENGTH: 21
<212> TYPE: RNA
<213> ORGANISM: Homo sapiens

<400> SEQUENCE: 50
uuaauaucgg acaaccauug u                                              21

<210> SEQ ID NO 51
<211> LENGTH: 22
<212> TYPE: RNA
<213> ORGANISM: Homo sapiens

<400> SEQUENCE: 51
uuguacaugg uaggcuuuca uu                                             22

<210> SEQ ID NO 52
<211> LENGTH: 22
<212> TYPE: RNA
<213> ORGANISM: Homo sapiens

<400> SEQUENCE: 52
gucauacacg gcucuccucu cu                                             22

<210> SEQ ID NO 53
<211> LENGTH: 22
<212> TYPE: RNA
<213> ORGANISM: Homo sapiens

<400> SEQUENCE: 53
gaauguugcu cggugaaccc cu                                             22

<210> SEQ ID NO 54
<211> LENGTH: 22
<212> TYPE: RNA
<213> ORGANISM: Homo sapiens

<400> SEQUENCE: 54
uauacaaggg caagcucucu gu                                             22
```

```
<210> SEQ ID NO 55
<211> LENGTH: 22
<212> TYPE: RNA
<213> ORGANISM: Homo sapiens

<400> SEQUENCE: 55
ugaaggucua cugugugcca gg                                                  22

<210> SEQ ID NO 56
<211> LENGTH: 20
<212> TYPE: RNA
<213> ORGANISM: Homo sapiens

<400> SEQUENCE: 56
ucccacuacu ucacuuguga                                                     20

<210> SEQ ID NO 57
<211> LENGTH: 22
<212> TYPE: RNA
<213> ORGANISM: Homo sapiens

<400> SEQUENCE: 57
uaugucugcu gaccaucacc uu                                                  22

<210> SEQ ID NO 58
<211> LENGTH: 21
<212> TYPE: RNA
<213> ORGANISM: Homo sapiens

<400> SEQUENCE: 58
ugagaugaag cacuguagcu c                                                   21

<210> SEQ ID NO 59
<211> LENGTH: 23
<212> TYPE: RNA
<213> ORGANISM: Homo sapiens

<400> SEQUENCE: 59
guccaguuuu cccaggaauc ccu                                                 23

<210> SEQ ID NO 60
<211> LENGTH: 21
<212> TYPE: RNA
<213> ORGANISM: Homo sapiens

<400> SEQUENCE: 60
cacauuacac ggucgaccuc u                                                   21

<210> SEQ ID NO 61
<211> LENGTH: 17
<212> TYPE: RNA
<213> ORGANISM: Homo sapiens

<400> SEQUENCE: 61
ggggcugggc gcgcgcc                                                        17

<210> SEQ ID NO 62
<211> LENGTH: 22
<212> TYPE: RNA
<213> ORGANISM: Homo sapiens

<400> SEQUENCE: 62
```
aucauacaag gacaauuucu uu                                            22

<210> SEQ ID NO 63
<211> LENGTH: 20
<212> TYPE: RNA
<213> ORGANISM: Homo sapiens

<400> SEQUENCE: 63
accaggaggc ugaggccccu                                               20

<210> SEQ ID NO 64
<211> LENGTH: 23
<212> TYPE: RNA
<213> ORGANISM: Homo sapiens

<400> SEQUENCE: 64 agcuggliguu gugaaucagg ccg                                          23

<210> SEQ ID NO 65
<211> LENGTH: 22
<212> TYPE: RNA
<213> ORGANISM: Homo sapiens

<400> SEQUENCE: 65
cacgcucaug cacacaccca ca                                            22

<210> SEQ ID NO 66
<211> LENGTH: 22
<212> TYPE: RNA
<213> ORGANISM: Homo sapiens

<400> SEQUENCE: 66
ccaccucccc ugcaaacguc ca                                            22

<210> SEQ ID NO 67
<211> LENGTH: 22
<212> TYPE: RNA
<213> ORGANISM: Homo sapiens

<400> SEQUENCE: 67
uauugcacuc gucccggccu cc                                            22

<210> SEQ ID NO 68
<211> LENGTH: 22
<212> TYPE: RNA
<213> ORGANISM: Homo sapiens

<400> SEQUENCE: 68
acaguagucu gcacauuggu ua                                            22

<210> SEQ ID NO 69
<211> LENGTH: 22
<212> TYPE: RNA
<213> ORGANISM: Homo sapiens

<400> SEQUENCE: 69
uauugcacuu gucccggccu gu                                            22

<210> SEQ ID NO 70
<211> LENGTH: 22
<212> TYPE: RNA
<213> ORGANISM: Homo sapiens

<400> SEQUENCE: 70

-continued uagcaccauc ugaaaucggu ua                                          22

<210> SEQ ID NO 71
<211> LENGTH: 22
<212> TYPE: RNA
<213> ORGANISM: Homo sapiens

<400> SEQUENCE: 71
uagcuuauca gacugauguu ga                                          22

<210> SEQ ID NO 72
<211> LENGTH: 22
<212> TYPE: RNA
<213> ORGANISM: Homo sapiens

<400> SEQUENCE: 72
aacccguaga uccgaacuug ug                                          22

<210> SEQ ID NO 73
<211> LENGTH: 22
<212> TYPE: RNA
<213> ORGANISM: Homo sapiens

<400> SEQUENCE: 73
uagcagcacg uaaauauugg cg                                          22

<210> SEQ ID NO 74
<211> LENGTH: 22
<212> TYPE: RNA
<213> ORGANISM: Homo sapiens

<400> SEQUENCE: 74
ucccugagac ccuaacuugu ga                                          22

<210> SEQ ID NO 75
<211> LENGTH: 23
<212> TYPE: RNA
<213> ORGANISM: Homo sapiens

<400> SEQUENCE: 75
agcuacauug ucugcugggu uuc                                         23

<210> SEQ ID NO 76
<211> LENGTH: 19
<212> TYPE: RNA
<213> ORGANISM: Homo sapiens

<400> SEQUENCE: 76
aauggauuuu uggagcagg                                              19

<210> SEQ ID NO 77
<211> LENGTH: 22
<212> TYPE: RNA
<213> ORGANISM: Homo sapiens

<400> SEQUENCE: 77
cauugcacuu gucucggucu ga                                          22

<210> SEQ ID NO 78
<211> LENGTH: 23
<212> TYPE: RNA
<213> ORGANISM: Homo sapiens

```
<400> SEQUENCE: 78
ugaggggcag agagcgagac uuu                                            23

<210> SEQ ID NO 79
<211> LENGTH: 21
<212> TYPE: RNA
<213> ORGANISM: Homo sapiens

<400> SEQUENCE: 79
uucacagugg cuaaguucug c                                              21

<210> SEQ ID NO 80
<211> LENGTH: 21
<212> TYPE: RNA
<213> ORGANISM: Homo sapiens

<400> SEQUENCE: 80
cuagacugaa gcuccuugag g                                              21

<210> SEQ ID NO 81
<211> LENGTH: 22
<212> TYPE: RNA
<213> ORGANISM: Homo sapiens

<400> SEQUENCE: 81
ugugacuggu ugaccagagg gg                                             22

<210> SEQ ID NO 82
<211> LENGTH: 22
<212> TYPE: RNA
<213> ORGANISM: Homo sapiens

<400> SEQUENCE: 82
ugagaacuga auuccauggg uu                                             22

<210> SEQ ID NO 83
<211> LENGTH: 22
<212> TYPE: RNA
<213> ORGANISM: Homo sapiens

<400> SEQUENCE: 83
ugagaacuga auuccauagg cu                                             22

<210> SEQ ID NO 84
<211> LENGTH: 23
<212> TYPE: RNA
<213> ORGANISM: Homo sapiens

<400> SEQUENCE: 84
caacggaauc ccaaaagcag cug                                            23

<210> SEQ ID NO 85
<211> LENGTH: 22
<212> TYPE: RNA
<213> ORGANISM: Homo sapiens

<400> SEQUENCE: 85
caugccuuga guguaggacc gu                                             22

<210> SEQ ID NO 86
<211> LENGTH: 24
<212> TYPE: RNA
<213> ORGANISM: Homo sapiens
```

```
<400> SEQUENCE: 86
ucccugagac ccuuuaaccu guga                                              24

<210> SEQ ID NO 87
<211> LENGTH: 23
<212> TYPE: RNA
<213> ORGANISM: Homo sapiens

<400> SEQUENCE: 87 agguacccg agcaacuuug cau                                                23

<210> SEQ ID NO 88
<211> LENGTH: 22
<212> TYPE: RNA
<213> ORGANISM: Homo sapiens

<400> SEQUENCE: 88
cucaguagcc aguguagauc cu                                                22

<210> SEQ ID NO 89
<211> LENGTH: 22
<212> TYPE: RNA
<213> ORGANISM: Homo sapiens

<400> SEQUENCE: 89
uaacacuguc ugguaaagau gg                                                22

<210> SEQ ID NO 90
<211> LENGTH: 22
<212> TYPE: RNA
<213> ORGANISM: Homo sapiens

<400> SEQUENCE: 90
gagcuuauuc auaaaagugc ag                                                22

<210> SEQ ID NO 91
<211> LENGTH: 22
<212> TYPE: RNA
<213> ORGANISM: Homo sapiens

<400> SEQUENCE: 91
uggaauguaa ggaagugugu gg                                                22

<210> SEQ ID NO 92
<211> LENGTH: 22
<212> TYPE: RNA
<213> ORGANISM: Homo sapiens

<400> SEQUENCE: 92
cgucuuaccc agcaguguuu gg                                                22

<210> SEQ ID NO 93
<211> LENGTH: 22
<212> TYPE: RNA
<213> ORGANISM: Homo sapiens

<400> SEQUENCE: 93
gagcuuuugg cccggguuau ac                                                22

<210> SEQ ID NO 94
<211> LENGTH: 22
<212> TYPE: RNA
```

<213> ORGANISM: Homo sapiens

<400> SEQUENCE: 94 uuugguccccc uucaaccagc ug				22

<210> SEQ ID NO 95
<211> LENGTH: 22
<212> TYPE: RNA
<213> ORGANISM: Homo sapiens

<400> SEQUENCE: 95
ugagguagua guuugugcug uu				22

<210> SEQ ID NO 96
<211> LENGTH: 22
<212> TYPE: RNA
<213> ORGANISM: Homo sapiens

<400> SEQUENCE: 96
ugagguagua gguugugugg uu				22

<210> SEQ ID NO 97
<211> LENGTH: 30
<212> TYPE: DNA
<213> ORGANISM: Homo sapiens

<400> SEQUENCE: 97
cctctgtctg ccttaacgtc ttcctgaatc			30

<210> SEQ ID NO 98
<211> LENGTH: 27
<212> TYPE: DNA
<213> ORGANISM: Homo sapiens

<400> SEQUENCE: 98
atgcagtgtg gaacacaatg aactgaa			27

<210> SEQ ID NO 99
<211> LENGTH: 25
<212> TYPE: DNA
<213> ORGANISM: Homo sapiens

<400> SEQUENCE: 99 cccccccactg ctaaatttga ctggc			25

<210> SEQ ID NO 100
<211> LENGTH: 28
<212> TYPE: DNA
<213> ORGANISM: Homo sapiens

<400> SEQUENCE: 100
cacaatgctg acactcaaac tgctgaca			28

<210> SEQ ID NO 101
<211> LENGTH: 23
<212> TYPE: DNA
<213> ORGANISM: Homo sapiens

<400> SEQUENCE: 101
cccccactgc taaatttgac tgg				23

<210> SEQ ID NO 102
<211> LENGTH: 31

```
<212> TYPE: DNA
<213> ORGANISM: Homo sapiens

<400> SEQUENCE: 102
cctctgtcgc tgatgtttct taagagtgag c                                     31

<210> SEQ ID NO 103
<211> LENGTH: 73
<212> TYPE: RNA
<213> ORGANISM: Homo sapiens

<400> SEQUENCE: 103
gcccagcuag cucagucggu agagcaugag acucuuaauc ucagggucau ggguuugagc      60
cccacguuug gug                                                         73

<210> SEQ ID NO 104
<211> LENGTH: 1236
<212> TYPE: DNA
<213> ORGANISM: Homo sapiens

<400> SEQUENCE: 104
tggatcgatg atgacttcca tatatacatt ccttggaaag ctgaacaaaa tgagtgaaaa      60
ctctatactg tcatcctcgt cgaactgagg tccagcacat tactccaaca ggggctagac     120
agagaaggcc aacatccgtt tgttgacatg ggttatatca aggcgtctgt tcaggcttag     180
aatgtggtct cttatgggtg atgggggtca caggagagtg gtggctccca tgtataggaa     240
atttcttgtt tgaaggactg tcagtgaggg tgggtaacac atgcattgtc tgcaggacta     300
ggtgaatgtc catgtggcct agcaagagtt agctggtagc ccgcctctgg ttgccaattt     360
gttcttgagt ccttgttctg ggttctcagg tcccacggag gaaaacagat ctgtgtggtt     420
gagaggtggg tacaaggccg catctttgtc atttgttggc taactttgtc cttggttgag     480
gacattagag ttttggtcac caggcatagc ctatgtgcct ttgtgcccgt gttgtatccc     540
acgtgttttg aggacatgta ttttgcacgt aaaggtgagc tcctgctcca agctggttct     600
gataccaaag gagtccctgg cttatcctaa actcatggta ggttaaagcc ttcctcctta     660
ggggttcagg gccgcaaggc ttttgtgagt ggcattgcag gcgttgaagc agtgatgttg     720
agagggatgg tcaatgtcag tgctcttttag caggatggtg tactgcaggg gcccccagcc     780
ccgagacgag catccctgca tccatgcatt tctgcctcca tgaacagggg aggccagaga     840
caggcagata gtagataaat tgcaggggac tggatgacat ggccctcgtg acctgtgcac     900
ctgtctgtct ttctgaagca cgcctgtgtt aactctgcac ctcccaggta gcactggcat     960
ggagggcagg cacatgttgg tgagggacaa ttgttacctt gtgtgagctg cggagatacc    1020
aggaagcccc tggacacaaa tggcaaaggc tccttcggaa gttgttggat cccttctgaa    1080
tgtaagcact tctttcccag agcactctga gtttcctcat ttgcagggac aaatactgtg    1140
cgtggatcga tgatgacttc cacatataca ttccttggaa agctgaacaa aatgagtgaa    1200
aactctatac cgtcatcctc gtcgaactga ggtcca                              1236

<210> SEQ ID NO 105
<211> LENGTH: 76
<212> TYPE: DNA
<213> ORGANISM: Homo sapiens

<400> SEQUENCE: 105
tggatcaatg atgagtatgc gtggggcatc tgaatcaaat attctgatta taccctgtct      60
```

```
gtatctctga ggtcca                                                      76

<210> SEQ ID NO 106
<211> LENGTH: 71
<212> TYPE: DNA
<213> ORGANISM: Homo sapiens

<400> SEQUENCE: 106
tggatcaatg atgagtaccc tggggtgtct gaatcttgga ttttgattaa accctataac      60
tctgaggtcc a                                                           71

<210> SEQ ID NO 107
<211> LENGTH: 106
<212> TYPE: DNA
<213> ORGANISM: Homo sapiens

<400> SEQUENCE: 107
gcgcagcgcc ctgtctccca gcctgaggtg cagtgctgca tctctggtca gttgggagtc      60
tgagatgaag cactgtagct caggaagaga gaagttgttc tgcagc                    106
```

STEM CELL-DERIVED EXOSOMES FOR THE TREATMENT OF CORNEAL SCARRING

CROSS-REFERENCE TO RELATED APPLICATIONS

This application is the National Stage of International Application No. PCT/US19/20516 (International Publication No. WO 2019/169380), filed on Mar. 4, 2019, which claims priority under Section 119(e) from U.S. Provisional Application Ser. No. 62/638,045 filed Mar. 2, 2018, entitled "STEM CELL-DERIVED EXOSOMES FOR THE TREATMENT OF CORNEAL SCARRING" the contents of which are incorporated herein by reference.

TECHNICAL FIELD

The present invention relates to compositions useful for treating corneal damage, and methods for making and using these compositions.

BACKGROUND OF THE INVENTION

Stem cells are undifferentiated cells having the ability to differentiate into two or more cell types with self-replication ability. Stem cells can be classified into totipotent stem cells, pluripotent stem cells, and multipotent stem cells depending upon differentiation potency thereof. In addition, stem cells can be classified into embryonic stem cells and adult stem cells depending upon biological origin. While embryonic stem cells are derived from preimplantation embryos, fetal reproductive organs in various stages of development, and the like, adult stem cells are derived from each organ, e.g., cornea, bone marrow, brain, liver, pancreas, or the like, of adults. Stem cells produce and secrete exosomes. Exosomes are small vesicles comprising specific constellations of polynucleotide and polypeptide cargos that are secreted by a variety of cell types. For example, corneal stromal stem cells produce exosomes comprising polynucleotide and polypeptide cargos that are specific to this cell lineage. As exosomes derived from stem cells contain polynucleotide (e.g. RNAs such as miRNAs) components as well as proteins, exosomes play important roles in intercellular communication.

Corneal stromal scars are the leading cause of corneal blindness and corneal blindness is the 2nd leading cause of blindness globally, with 4.1 million people blinded in both eyes and people million are blinded in one eye. The conventional treatment for restoring vision in people who have stromal scarring is corneal transplantation. Unfortunately, however, due to the severe shortage of transplantable cornea tissues, more than 95% of the people affected by stromal scarring remain blinded.

It is anticipated that therapies using exosomes or their active agents may be useful in new paradigms designed to address various pathological conditions such as corneal scaring and overcome limitations in existing therapies. However, challenges in this technology include the limited availability of exosomes, and the fact that the components of exosomes are not clearly defined.

SUMMARY OF THE INVENTION

The present invention provides alternatives to conventional therapies such as corneal transplantation for the treatment of corneal scarring. As discussed below, embodiments of the invention include methods and materials useful to deliver therapeutic agents such as exosomes or active exosome components to corneal tissue. In view of the shortage of transplantable cornea tissues, these methods and associated materials are more feasible and cost-effective than the conventional therapy of corneal transplantation. In certain embodiments of the invention, primary stem cells are used to obtain exosome materials useful in embodiments of the invention. In other embodiments of the invention, the stem cells used to obtain exosomes (and/or active exosome components) are an immortalized cell line. Immortalized corneal stromal stem cells as disclosed herein offer an unlimited supply of exosomes (and/or active exosome components) useful for the treatment of certain pathological conditions such as corneal scar therapy.

Embodiments of the invention include compositions and methods useful in the treatment of a number of pathological conditions such as corneal epithelial defects, persistent sterile corneal ulcers, neurotrophic corneal ulcers, keratoconus, as well as corneal scarring due to bacterial or viral keratitis. In this context, certain characteristics of the invention have the potential to revolutionize the treatment of corneal scarring. In particular, exosome therapy has great promise as the administration of exosomes in a therapeutic regimen does not require an operating room, and consequently can be practiced by general practitioners instead of being limited to corneal surgeons. This will, for example, make treatments for corneal scarring more accessible in developing parts of the world.

The data presented herein shows that polynucleotides found in exosomes such as those produced by corneal stromal stem cells and certain other stem cells (see, e.g., the data in FIG. 5) have the ability to reduce existing corneal scars and prevent scar formation. The invention disclosed herein is based upon these discoveries and has a number of embodiments. Embodiments of the invention include methods of making therapeutic compositions (e.g. for the treatment of corneal scarring) using the exosome and/or active exosome components disclosed herein. One such embodiment is a method of making a pharmaceutical composition comprising combining together in an aqueous formulation at least 1, 5 10, 20, 30, 40 or 50 of the polynucleotides selected from SEQ ID NO: 1-SEQ ID NO: 107; and one or more pharmaceutical excipients selected from the group consisting of a preservative, a tonicity adjusting agent, a detergent, a viscosity adjusting agent, a sugar or a pH adjusting agent. In typical embodiments of the invention, the polynucleotides are disposed within one or more exosomes; the pharmaceutical composition comprises an excipient selected for use in ocular administration; and/or the exosomes further comprise a plurality of expression products of one or more genes shown in Table 2. In certain embodiments of the invention, the exosomes are disposed in a hydrogel.

Another embodiment of the invention is a pharmaceutical composition comprising exosomes (or exosome active agents) such as those produced corneal stromal stem cells, wherein the compositions include a plurality of polynucleotides in Table 1 in combination with a pharmaceutical excipient such as a preservative, a tonicity adjusting agent, a detergent, a viscosity adjusting agent, a sugar (e.g. trehalose) or a pH adjusting agent. In certain embodiments, the compositions are formed to a constellation of polynucleotides such as at least 10, 20 or all of the polynucleotides in Table 1; and at least 10, 20 or more expression products of the genes shown in Table 2. In some embodiments, exosomes are selected to be those that express a constellation of polypeptides (e.g. proteins) in combination with the polynucleotides disclosed herein. In certain embodiments of the invention, the composition further comprises a hydrogel in which the constituents such as exosomes are disposed (e.g. a collagen, fibrin, polyphenylene sulfide or hyaluronic acid hydrogel etc.). In specific embodiments of the invention the composition comprises excipients useful in compositions formulated for ocular administration such as direct injection into the corneal stroma.

Another embodiment of the invention is a method of delivering exosomes (and/or active exosome components such as the polynucleotides in Table 1) into cells of corneal tissue. Typically, these methods are practiced on corneal cells present in an individual having corneal epithelial defects, persistent sterile corneal ulcers, neurotrophic corneal ulcers, keratoconus, or corneal scarring due to bacterial or viral keratitis. These methods comprise contacting a pharmaceutical composition as disclosed herein with the corneal tissue so that the polynucleotides (e.g. ones disposed in exosomes) are internalized into cells of the tissue, thereby delivering the polynucleotides into the corneal tissue cells. Typically in these methods, exosomes are used that are selected to express a plurality of polynucleotides in Table 1 and/or a plurality of expression products of the genes shown in Table 2. In some embodiments of these methods, the composition is delivered by direct injection into the corneal stroma. In other embodiments of these methods, the composition is delivered by coating an exosome containing hydrogel in the inner surface of a contact lens and contacting an eye with the contact lens.

Yet another embodiment of the invention comprises immortalized corneal stromal stem cell lines, wherein the corneal stromal stem cell line forms exosomes that comprise a plurality of polynucleotides in Table 1 and/or a plurality of expression products of the genes shown in Table 2. High quality exosomes having defined properties can be produced consistently from such immortalized corneal stromal stem cells (e.g. exosomes that comprise a plurality of polynucleotides in Table 1 and/or a plurality of expression products of the genes shown in Table 2).

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 3A shows data on Col3a1 expression. FIG. 3B shows data on Fneda expression. FIG. 3C shows data on Has2 expression. FIG. 3D shows data on Acta2 expression. FIG. 3E shows data on Sparc expression. FIG. 3F shows data on TenC expression.

As shown in FIG. 4B, the level of the genes associated with fibrosis were significantly reduced in the exosome treated eyes at the same level achieved using CSSCs. Therefore, when exosomes are generated from immortalized CSSCs, the quantity and quality could be controlled better. It is feasible to be further developed into a therapeutic for the treatment of existing scar and prevent scarring in active keratitis.

FIG. 6 provides a table showing miRNA polynucleotides useful in embodiments of the invention (e.g. those that are highly and differentially expressed in CSSC derived exosomes having therapeutic properties). The first column shows the name/designation of the polynucleotide. The second and third columns show data from CSSC and HEK cells. The fourth column shows p values. The final column lists PMIDs—referring to a publication in which this specific miRNA was listed. See also Table 1 below.

DETAILED DESCRIPTION OF THE INVENTION

Figure 1:
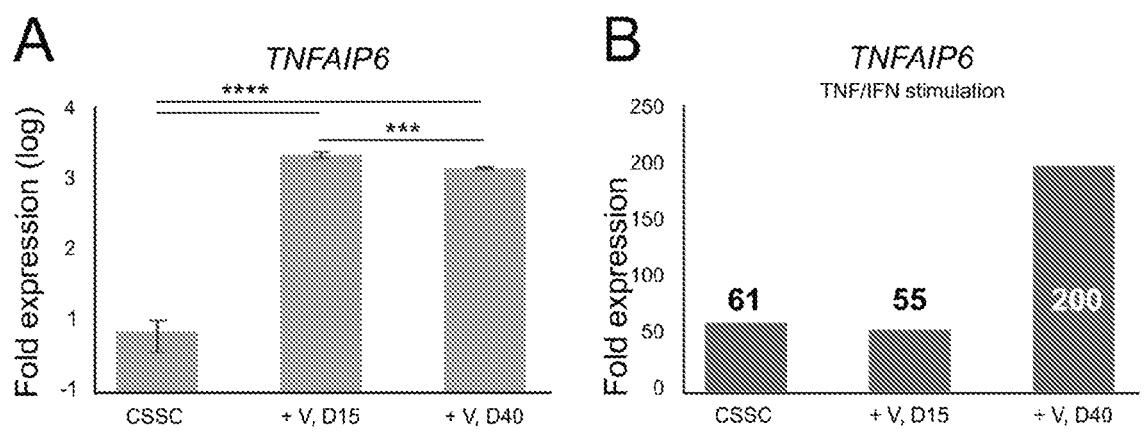
FIGS. 1A and 1B provide graphed data showing fold expression of TNFAIP6 after treatment overnight with hIFN-γ and hTFN-α (FIG. 1B) compared to the untreated cells (FIG. 1A) for each cell line. Fold expression normalized to the respective control cells. ANOVA, Tukey's for multiple comparison test; **$p<0.0001$; *$p<0.005$; **$p<0.01$; *$p<0.05$.

In the description of embodiments, reference may be made to the accompanying figures which form a part hereof, and in which is shown by way of illustration a specific embodiment in which the invention may be practiced. It is to be understood that other embodiments may be utilized and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. All publications mentioned herein are incorporated herein by reference to disclose and describe aspects, methods and/or materials in connection with the cited publications.

ASPECTS AND EMBODIMENTS OF THE INVENTION

The corneal stroma is being increasingly recognized as a repository for useful stem cells. Like the limbal and endothelial niches, stromal stem cells often reside in the peripheral cornea and limbus. These peripheral and limbal corneal stromal cells (PLCSCs) are known to produce mesenchymal stem cells in vitro. Corneal stromal stem cells (CSSC), or limbal mesenchymal stem cells have the potential to reduce cornea scars when applied topically after wounding. Unfortunately, CSSCs have a limited life span in culture, and the ability for repair is inversely correlated to the number of passages in vitro. In addition, CSSCs isolated from different donors have different level of efficiency to reduce corneal scarring. These shortcomings of primary CSSCs pose limitations that make it difficult to translate what is know in this art into clinical applications.

Embodiments of the invention include corneal stromal stem cells (CSSCs), adipose derived stem cells (ADSC), umbilical cord stem cells (UC), or bone marrow derived stem cells (BDMSC), to exosomes and their active agents produced by such cells, and methods for making and using such cells, exosomes and exosome active agents. Exosomes are small vesicles, typically between 50-500 nm in diameter, that are secreted by a number of different cell types for communicating with other cells via the proteins and nucleic acids they carry. Depending on their cellular origin, exosomes carry a uniquely distinct profile of proteins and polynucleotides, which can trigger signaling pathways in other cells and/or transfer exosomal products into other cells by exosomal fusion with cellular plasma membranes. Exosomes can mediate intercellular communication by transferring membrane and cytosolic proteins, lipids, and RNAs between cells. These transferred molecules are functional in the recipient cells.

As disclosed herein, exosomes derived from corneal stromal stem cells (CSSCs), adipose derived stem cells (ADSC), umbilical cord stem cells (UC), or bone marrow derived stem cells (BDMSC) have been discovered to have the ability to reduce the scar in a mouse model of corneal wounding. In this context, aspects of the invention disclosed herein include the identification of agents having therapeutic potential for pathologies such as corneal scarring. Illustrative embodiments of the invention include these stem cells and exosomes (and/or active exosome components) obtainable from these cells. An illustrative embodiment described herein are exosome compositions derived from a corneal stromal stem cell (CSSC). The exosomes (and/or active exosome components) may be derivable from the CSSC by any of several means, for example by secretion, budding or dispersal of exosomes from the CSSC. Optionally, active components of the exosomes are then separated/purified from the exosomes. Embodiments of the invention include methods of using the exosomes to deliver polynucleotides to a cell, for example in therapeutic methods designed to treat corneal scarring.

Further embodiments and aspects of invention are discussed in the following sections.

Immortalized Corneal Stromal Stem Cell Lines

Embodiments of the invention include immortalized corneal stem cell lines that produce exosomes selected to comprise certain polynucleotides such as that those identified in Table 1. As disclosed herein, we have developed working embodiments of CSSC lines immortalized using a lentiviral construction overexpressing the oncogene cMYC, SV40 antigent or the telomerase reverse transcriptase (TERT). The immortalization of the CSSCs offers the possibility for constant supply of exosomes having defined properties, less variability in the exosome production, elimination of variation of donors and a safe technology for corneal wounding repair.

Figure 2:
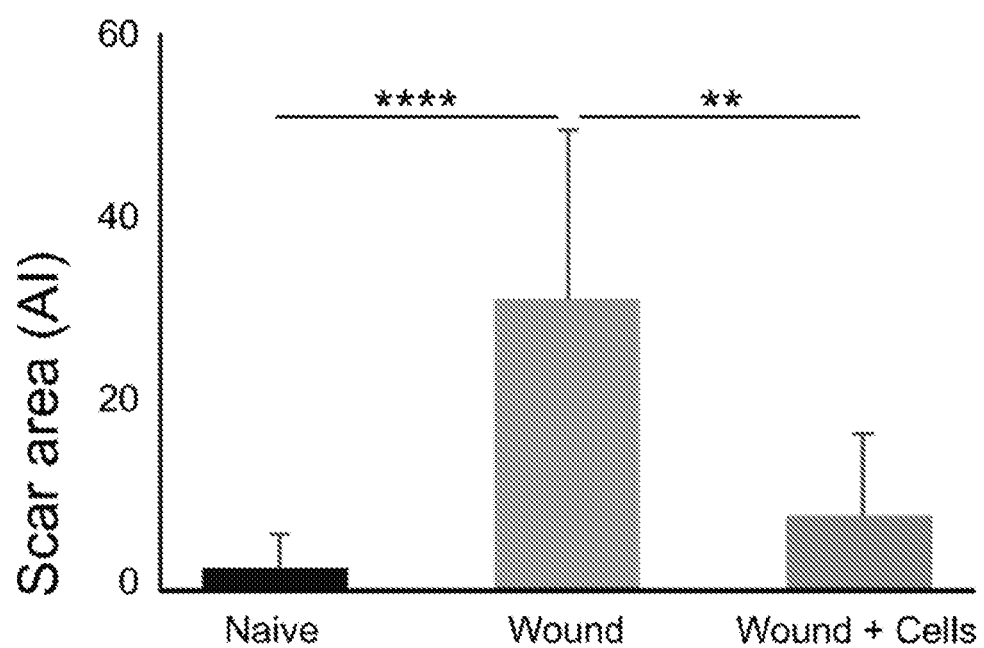
FIG. 2 provide graphed data showing corneal scar area analysis in the control (naïve) after wounding (Wound) with or without application of the corneal stromal stem cell (CSSC) immortalized cells (Wound+cells) after 15 days. ANOVA, Tukey's for multiple comparison test; **$p<0.0001$; *$p<0.005$; **$p<0.01$; *$p<0.05$.
Figure 3:
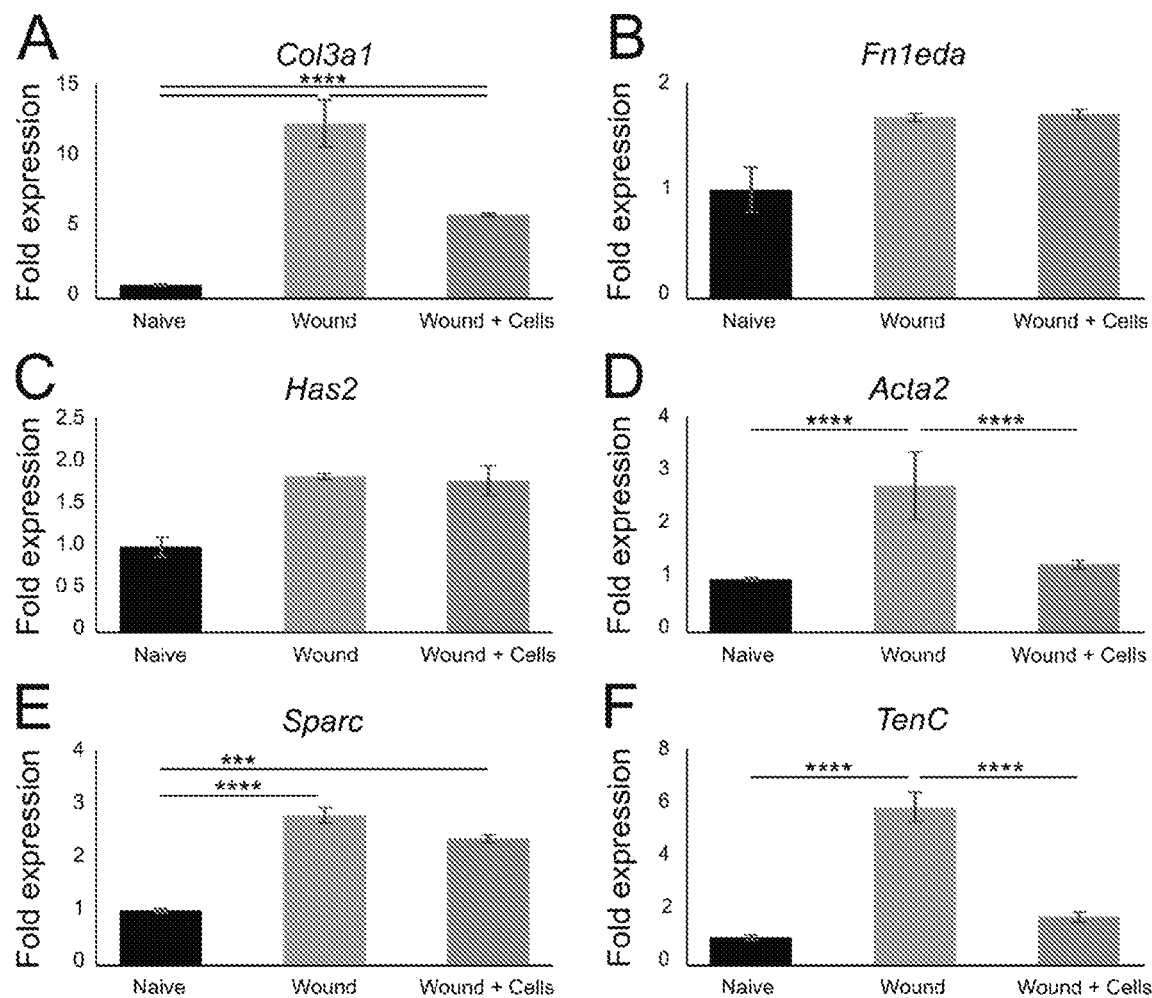
FIGS. 3A-3F provide graphed data showing gene expression analysis of the corneas in the control (naïve) after wounding (Wound) with or without application of the CSSC immortalized cells (Wound+cells) after 15 days. ANOVA, Tukey's for multiple comparison test; **$p<0.0001$; *$p<0.005$; **$p<0.01$; *$p<0.05$.

Our immortalized CSSC cell lines showed a similar gene expression profile than the original cell line. Furthermore, the immortalized cells responded in the same way to inflammation as observed with TSG-6 mRNA expression (FIG. 1) which was shown to correlated to the capacity for wound repair. In addition to the reduction of the scar area, the expression of fibrotic genes was decreased accordingly (FIGS. 2 and 3). Indeed, compared to the wounded corneas, the immortalized cells demonstrated a reduction of the scar area (FIG. 2), as well as downregulation of fibrosis-associated genes such as Acta2, Col3a1 and TenC (FIG. 3). CSSCs have been showed to reduce existing corneal scars and reduce scar formation in active sterile keratitis in humans. Therefore, immortalized human CSSCS and/or the exosomes produced by such cells can be useful as therapeutics for reducing corneal scars in humans.

Stem Cell Conditioned Medium (CSSC-CM)

Embodiments of the invention include cultured media from corneal stromal stem cells (CSSC), adipose derived stem cells (ADSC), umbilical cord stem cells (UC), or bone marrow derived stem cells (BDMSC). Conditioned cell culture medium such as a Corneal Stromal Stem Cell Conditioned Medium (CSSC-CM) may be obtained by culturing a corneal stromal stem cell (CSSC) such as primary corneal stromal stem cells or the immortalized lines disclosed herein, a descendent thereof or a cell line derived therefrom in a cell culture medium; and isolating the cell culture medium. The cell, or a descendent thereof, may be propagated in the absence of co-culture in a serum free medium. While corneal stromal stem cells are used as the typical embodiment in descriptions of the invention, in addition to corneal stromal stem cells (CSSCs), embodiments of the invention relate to conditioned media from adipose derived stem cells (ADSC), umbilical cord stem cells (UC), or bone marrow derived stem cells (BDMSC). See, e.g. the data presented in FIG. 5.

The term "cell-free CSSC (or other cell type disclosed herein)-conditioned medium", as used herein, refers to a medium substantially free of cells which has been contacted with the CSSC in culture. The term "medium" or "culture medium", as used herein, refers to any substance or preparation used for the cultivation of living cells, including the components of the environment surrounding the cells. The medium can be any medium adequate for culturing CSSC, for example Dulbecco's Modified Eagle's Medium (DMEM), with antibiotics (for example, 100 units/ml Penicillin and 100 μg/ml Streptomycin) or without antibiotics, and 2 mM glutamine, and supplemented with 2%-20% fetal bovine serum (FBS). In a particular embodiment, the CSSC-conditioned medium does not comprise any type of sera, including fetal bovine serum, bovine serum (BS), calf serum (CS), fetal calf serum (FCS), newborn calf serum (NCS), goat serum (GS), horse serum (HS), porcine serum, sheep serum, rabbit serum, rat serum (RS).

Embodiments of the invention comprise cell-free CSSC-conditioned medium. In illustrative embodiments of the invention, the CSSC-conditioned medium has been contacted with the CSSC culture (e.g. cell at about an 80% confluence) for at least 1 hour, at least 2 hours, at least 6 hours, at least 12 hours, at least 24 hours, at least 2 days, at least 3 days, at least 4 days, at least 5 days or more. In a more particular embodiment, the CSSC-conditioned medium has been contacted with the CSSCs for 3 or 4 days. The cell-free CSSC-conditioned medium can be obtained by any method known by the skilled person that allows recovering a culture medium without the cells. For example, the medium can be collected from a monolayer culture of CSSCs. In a particular embodiment, the cell-free CSSC conditioned medium is obtained by collecting the medium from CSSCs culture, centrifuging said medium in order to remove cells and debris and collecting the supernatant. In a more particular embodiment, cells and debris are removed by subjecting the medium to centrifugation. In an even more particular embodiment, these centrifugations are performed at 4° C. The method of can comprise filtering a cell-free CSSC-conditioned medium using a kDa cut-off membrane and recovering the retentate. The term "filtering", as used herein, means making the CSSC-conditioned media to pass through the membrane. The method can further comprise centrifuging the cell-free CSSC-conditioned medium at a speed sufficient to precipitate exosomes and recovering the pellet. In a particular embodiment, the CSSCs are human.

In other working embodiments of the invention, exosome extracellular vesicles are excreted from the cell culture medium after 48 h incubation with the cells at 80% confluence. The exosomes are isolated after a first step involving affinity binding of the exosomes to polymers (total exosome isolation solution, Life Technologies). Then, the exosomes are purified with a 2-step centrifugation protocol, e.g. 1 hour at 12,000 g and then 2 hours at 130,000 g. Pellets containing the exosomes are then resuspended in 300 ul PBS. Other method of isolation that employs serial filtration, tangential flow filtration (TFF), with or without a sucrose gradient sedimentation or size-exclusion chromatography.

Stem Cell Exosomes

Exosomes are classically defined as "saucer-like" vesicles or a flattened sphere limited by a lipid bilayer with diameters of 50-500 nm and are formed by inward budding of the endosomal membrane. Exosomes are typically enriched in cholesterol and sphingomyelin, and lipid raft markers. The molecular composition of exosomes from different cell types and of different species has been examined. In general, exosomes contain ubiquitous proteins that appear to be common to all exosomes and proteins that are cell-type specific. Also, proteins in exosomes from the same cell-type but of different species are highly conserved. The ubiquitous exosome-associated proteins include cytosolic proteins found in cytoskeleton e.g. tubulin, actin and actin-binding proteins, intracellular membrane fusions and transport e.g. annexins and rab proteins, signal transduction proteins, and metabolic enzymes.

Exosomes from different cell lineages are also known to comprise different constellations of polypeptides as well as polynucleotides such as mRNA and microRNA, molecules which can be delivered to another cell, and can be functional in this new location. In this context, embodiments of the invention provide exosomes (and/or active exosome components) produced by corneal stromal stem cells (CSSCs), adipose derived stem cells (ADSC), umbilical cord stem cells (UC), or bone marrow derived stem cells (BDMSC), for example, those found in a medium which is conditioned by culture of CSSCs. The exosome comprise molecules secreted by these cells. Such exosomes, and combinations of any of the molecules comprised therein, including in particular polynucleotides or proteins, may be used to supplement the activity of, or in place of, the CSSCs (or other cell types), the medium conditioned by the CSSCs for the purpose of for example treating or preventing a disease such a corneal scarring.

The exosomes (and/or active exosome components) of the invention have at least one property of a corneal stromal stem cell that is associated with healing corneal scarring. The exosome typically has multiple biological activities of an CSSC. The exosome may for example have a therapeutic or restorative activity of an CSSC. The exosome may be produced, exuded, emitted or shed from stem cells such as CSSC. Where the cell such as a CSSC is in cell culture, the exosome may be secreted into the cell culture medium. The exosomes may be formed by inward budding of the endosomal membrane. The exosomes may comprise one or more polynucleotides or proteins present in corneal stromal stem cells or corneal stromal stem cell conditioned medium (CSSC-CM), such as a protein characteristic or specific to the CSSC or CSSC-CM. They may comprise RNA, for example miRNA. Illustrative polynucleotides present in the exosomes of the invention include those shown in Table 1, optionally in combination with a plurality of expression products of the genes shown in Table 2.

The exosome may be produced or isolated in a number of ways. One such method comprises isolating the exosome from a corneal stromal stem cell (CSSC). Such a method may comprise isolating the exosome from a corneal stromal stem cell conditioned medium (CSSC-CM). The exosome may be isolated for example by being separated from non-associated components based on any property of the exosome. For example, the exosome may be isolated based on molecular weight, size, shape, composition or biological activity.

To isolate exosomes, the conditioned medium may be filtered or concentrated or both during, prior to or subsequent to separation. For example, it may be filtered through a membrane, for example one with a size or molecular weight cut-off. It may be subject to tangential force filtration or ultrafiltration. For example, filtration with a membrane of a suitable molecular weight or size cutoff, may be used. The conditioned medium, optionally filtered or concentrated or both, may be subject to further separation means, such as column chromatography. For example, high performance liquid chromatography (HPLC) with various columns may be used. The columns may be size exclusion columns or binding columns.

One or more properties or biological activities of the exosome may be used to track its activity during fractionation of the corneal stromal stem cell conditioned medium (CSSC-CM). As an example, light scattering, refractive index, dynamic light scattering or UV-visible detectors may be used to follow the exosomes. In addition, a therapeutic property such as corneal healing activity may be used to track the activity during fractionation.

Figure 5:
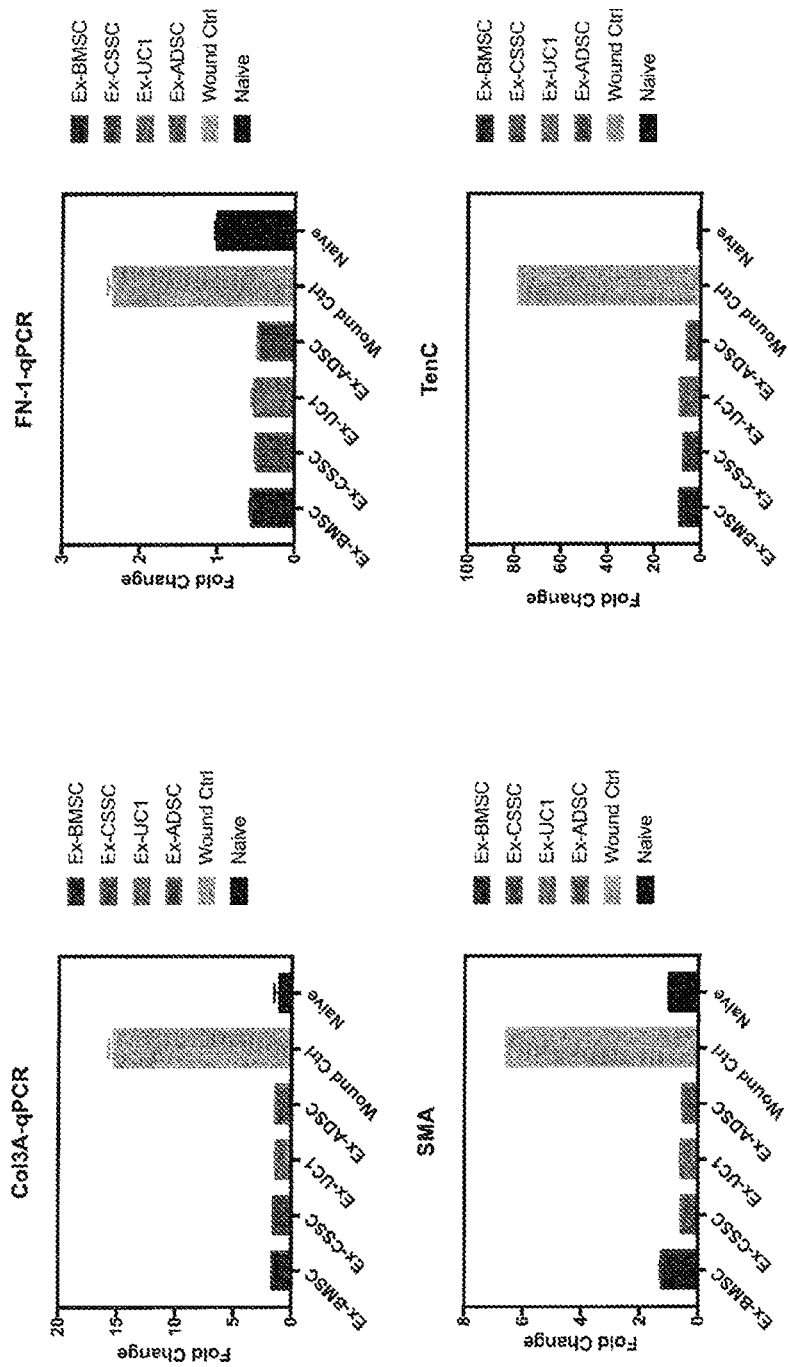
FIGS. 5A-5D provide graphed data showing how exosomes from Non-Corneal Mesenchymal Stem Cells Suppress Corneal Fibrosis. In these studies mouse corneal debridement wounds were treated with equal numbers of exosomes produced by corneal stromal stem cells (Ex-CSSC), bone marrow derived stem cells (Ex-BMSC), umbilical cord derived stem cells (Ex-UC1), or adipose derived stem cells (Ex-ADSC) (all from human sources). After 14 days of healing, RNA from wounded corneas was analyzed for expression of fibrotic genes for collagen 3 (Col3A, FIG. 4A), fibronectin (FN-1, FIG. 4B), smooth muscle actin (SMA, FIG. 4C) and tenascin C (TenC, FIG. 4D). The expression levels were compared to that of non-wounded cornea (Naive) and of corneas that were wounded but not treated (Wound Control). Exosomes from all sources suppressed the fibrotic expression. (n=3, $p<0.05$). These specific non-corneal stem cells exosomes appear equally active as CSSC exosomes.

The following paragraphs provide a specific example of how a corneal stromal stem cell exosome may be obtained, and this example can be adapted to the other stem cells having the properties disclosed herein (see, e.g. FIG. 5). A corneal stromal stem cell exosome may be produced by culturing corneal stromal stem cells in a medium to condition it. The corneal stromal stem cells (or adipose derived stem cells, umbilical cord stem cells, or bone marrow derived stem cells) may comprise immortalized cells. The medium may comprise DMEM. The medium may be supplemented with conventional agents such as insulin, transferrin, or selenoprotein (ITS), or any combination thereof. It may comprise growth factors such as FGF2 or PDGF. The medium may also comprise glutamine-penicillin-streptomycin or any combination thereof.

The cells may be cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more.

The conditioned medium may be subject to liquid chromatography such as HPLC. The conditioned medium may be separated by size exclusion. Any size exclusion matrix such as Sepharose may be used. As an example, a TSK Guard column SWXL, 6X.40 mm or a TSK gel G4000 SWXL, 7.8×300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector. Fractions which are found to exhibit dynamic light scattering may be retained.

Pharmaceutical Compositions of the Invention

Compositions comprising the polynucleotides, polypeptides and exosomes of the invention can be formulated as pharmaceutical compositions in a variety of forms adapted to the chosen route of administration, for example, in an ocular infusion. The compounds of the invention may be topically administered, e.g., in combination with a pharmaceutically acceptable vehicle such as an inert diluent. For compositions suitable for administration to humans, the term "excipient" is meant to include, but is not limited to, those ingredients described in Remington: The Science and Practice of Pharmacy, Lippincott Williams & Wilkins, 21st ed. (2006) the contents of which are incorporated by reference herein.

The compounds may also be administered in a variety of ways, for example intraocularly. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

Useful liquid carriers include water, alcohols or glycols or water/alcohol/glycol blends, in which the compounds can be dissolved or dispersed at effective levels, optionally with the aid of non-toxic surfactants. Adjuvants such as additional antimicrobial agents can be added to optimize the properties for a given use.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months.

In certain embodiments of the invention, exosomes or active components found in such exosomes such as those shown in Tables 1 and 2 (e.g. which are purified from the exosomes or synthesized in vitro) may be used for the preparation of a pharmaceutical composition for the treatment of disease. Such disease may comprise a disease treatable by regenerative therapy, including corneal scarring. The term "pharmaceutical composition", as used herein, refers to a composition comprising a therapeutically effective amount of active agents of the present invention and at least one non-naturally occurring pharmaceutically acceptable excipient. Embodiments of the invention relate to pharmaceutical compositions comprising an exosome, isolated exosome population or isolated exosome materials in combination with a pharmaceutically acceptable excipient.

The terms "pharmaceutically acceptable excipient", or "pharmaceutically acceptable carrier," "pharmaceutically acceptable diluent,", or "pharmaceutically acceptable vehicle," used interchangeably herein, refer to a non-toxic solid, semisolid or liquid filler, diluent, encapsulating material or formulation auxiliary of any conventional type. A pharmaceutically acceptable carrier is essentially non-toxic to recipients at the dosages and concentrations employed and is compatible with other ingredients of the formulation. Suitable carriers include, but are not limited to water, dextrose, glycerol, saline, ethanol, and combinations thereof. The carrier can contain additional agents such as wetting or emulsifying agents, pH buffering agents, or adjuvants which enhance the effectiveness of the formulation.

The person skilled in the art will appreciate that the nature of the excipient in the pharmaceutical composition of the invention will depend to a great extent on the administration route. In the case of the pharmaceutical compositions formulated for their topical use, a pharmaceutical composition according to the invention normally contains the pharmaceutical composition of the invention mixed with one or more pharmaceutically acceptable excipients. These excipients can be, for example, inert fillers or diluents, such as sucrose, sorbitol, sugar, mannitol, microcrystalline cellulose, starches, including potato starch, calcium carbonate, sodium chloride, lactose, calcium phosphate, calcium sulfate or sodium phosphate; crumbling agents and disintegrants, for example cellulose derivatives, including microcrystalline cellulose, starches, including potato starch, sodium croscarmellose, alginates or alginic acid and chitosans; binding agents, for example sucrose, glucose, sorbitol, acacia, alginic acid, sodium alginate, gelatin, starch, pregelatinized starch, microcrystalline cellulose, aluminum magnesium silicate, sodium carboxymethylcellulose, methylcellulose, hydroxypropyl methylcellulose, ethylcellulose, polyvinylpyrrolidone, polyvinyl acetate or polyethylene glycol, and chitosans; lubricating agents, including glidants and antiadhesive agents, for example magnesium stearate, zinc stearate, stearic acid, silicas, hydrogenated vegetable oils or talc.

In a particular preferred embodiment, the pharmaceutical compositions of the invention are formulated as an ophthalmic formulation for administration to the eye and for this reason have formulation elements specifically selected for this purpose. For example, the most widely used ophthalmic buffer solutions are boric acid vehicle and Sorensen's modified phosphate buffer. The boric acid vehicle is a 1.9% solution of boric acid in purified water or preferably sterile water. It is isotonic with tears. It has a pH of approximately 5 and is useful when extemporaneously compounding ophthalmic solutions of drugs that are most stable at acid pH. Optionally, the buffer solution is convenient to use as a tonicity adjustor. In circumstances when an ophthalmic solution without a buffer is desired, any compatible salt or non-electrolyte that is approved for ophthalmic products may be used. Sodium chloride, sodium nitrate, sodium sulfate, and dextrose are common neutral tonicity adjustors.

The use of preservatives is common in ophthalmic solutions in order to prevent the growth of, or to destroy, microorganisms accidentally introduced when the container is opened during use. Benzyl alcohol, thimerisol and the parabens are the preservatives commonly found in ophthalmic solutions. In addition, certain active ingredient(s) may be susceptible to oxidative degradation. If oxidation is a problem, an antioxidant can be included. Sodium metabisulfite and Sodium bisulfite are acceptable for this purpose in drug preparations. Finally, an increase in the viscosity of ophthalmic products will result in a longer residence time in the eye, providing a longer time for drug absorption and effect. Numerous viscosity enhancing materials can be used, among which methylcellulose is a common example.

As noted above, embodiments of the invention include pharmaceutical compositions comprising exosomes (and/or selected active components derived therefrom such as those shown in Tables 1 and 2) produced by an immortalized corneal stromal stem cell line, wherein the exosomes are selected to comprise a plurality of polynucleotides in Table 1 in combination with a pharmaceutical excipient such as a preservative, a tonicity adjusting agent, a detergent, a viscosity adjusting agent, a sugar (e.g. trehalose) or a pH adjusting agent. In certain embodiments of the exosomes are further selected to comprise a constellation of polynucleotides such as at least 10, 20 or all of the polynucleotides in Table 1.

As noted above, embodiments of the invention include pharmaceutical compositions comprising exosomes produced by corneal stromal stem cells, wherein the exosomes are selected to comprise a plurality of polynucleotides in Table 1 in combination with a pharmaceutical excipient such as a preservative, a tonicity adjusting agent, a detergent, a viscosity adjusting agent, a sugar (e.g. trehalose) or a pH adjusting agent. In certain embodiments of the exosomes are further selected to comprise a constellation of polynucleotides such as at least 10, 20 or all of the polynucleotides in Table 1; and/or a plurality of expression products of the genes shown in Table 2. In some embodiments of the invention, the corneal stromal stem cells from which the exosomes (and/or active exosome components) are derived is an immortalized cell line.

In certain embodiments of the invention, the composition further comprises a hydrogel in which the exosomes are disposed (e.g. a collagen, a fibrin, polymers such as a polyphenylene sulfide, amniotic membrane or a hyaluronic acid hydrogel). Hydrogels used in similar contexts are known in the art and can be adapted for use with the compositions disclosed herein. See, e.g. Kalaiselvi et al., Burdick et al., Adv Mater. 2011 March 25; 23(12): H41-H56, Pape et al., Journal of Visualized Experiments June 2015 (100) e52450, 1-8, Shi et al., Front. Physiol., 7 Nov. 2017.

In certain specific embodiments of the invention the composition comprises excipients used in compositions formulated for direct injection into the corneal stroma (see, e.g. Kalaiselvi et a1. Br J Ophthalmol 2015; 99:195-198 and Tu et al., Cornea 2014, 33:990-993). In some embodiments of the invention, the composition coats a vehicle used to introduce the composition into an eye of a patient having corneal scarring, for example a contact lens (see, e.g. Schultz et al., Clin Exp Optom 2010; 93: 2: 61-65 and Guzman-Aranguez et al., JOURNAL OF OCULAR PHARMACOLOGY AND THERAPEUTICS Volume 29, Number 2, 2013, 189-199).

As noted above, embodiments of the invention include methods of making therapeutic compositions (e.g. for the treatment of corneal scarring) using exosomes and/or active exosome components (e.g. microRNA polynucleotides) disclosed herein. One such embodiment is a method of making a pharmaceutical composition comprising combining together in an aqueous formulation at least 1, 5 10, 20, 30, 40, 50 or more of the polynucleotides comprising a sequence of SEQ ID NO: 1-SEQ ID NO: 107; and one or more pharmaceutical excipients selected from the group consisting of a preservative, a tonicity adjusting agent, a detergent, a viscosity adjusting agent, a sugar or a pH adjusting agent. Certain embodiments of the invention include making a pharmaceutical composition having selected constellation of polynucleotides such as a pharmaceutical composition comprising polynucleotides comprising SEQ ID NO: 1-SEQ ID NO: 17, or SEQ ID NO: 1-SEQ ID NO: 43, or SEQ ID NO: 1-SEQ ID NO: 48, or SEQ ID NO: 1-SEQ ID NO: 94, or SEQ ID NO: 1-SEQ ID NO: 107. In addition, some embodiments of the invention are selected to focus on at least 5, 10, 20, 30 or 40 microRNAs (abbreviated miR), small non-coding RNA molecule sequences of SEQ ID NO: 1-SEQ ID NO: 107.

In typical embodiments of the invention, the polynucleotides are disposed within a population of exosomes; and/or the pharmaceutical composition comprises an excipient selected for use in ocular administration; and/or the exosomes further comprise a plurality of expression products of 10, 20, 30, 40, 50 or more genes shown in Table 2. In certain embodiments of the invention, the population of exosomes is disposed within a hydrogel.

Delivery Polynucleotides Such as miRNAs to Corneal Tissues

A pressing problem in treatment therapeutic regimens that comprise polynucleotides such as miRNAs is getting target cells to efficiently absorb and incorporate the desired polynucleotides. In this context, some embodiments of the invention will effectively deliver therapeutic polynucleotides such as miRNAs to tissue or other locations within a subject for treatment. Polynucleotides such as MiRNAs can regulate gene expression in cells, and can be used for therapeutic benefit. For example, miRNAs can be used to promote corneal tissue regeneration/healing.

Embodiments of the invention include polynucleotide (e.g. miRNA) delivery systems and methods for making and using them. While miRNAs are discussed as typical examples, the following methods encompass other polynucleotides as well. Without limitation to only those embodiments expressly disclosed herein and without disclaiming any embodiments or subject matter, some embodiments comprise a miRNA delivery system whereby miRNA expression is modified in target exosome-producing cells (as one nonlimiting example, immortalized CSSCs), and exosomes or other vesicles, miRNAs from those cells, and/or those cells themselves, are used as delivery vehicles to deliver therapeutic miRNA(s) into cells, tissue, or organs. Some embodiments comprise the therapeutic administration and use of such induced cells to treat mammalian injuries and diseases, including but not limited to, corneal scarring. In some embodiments, such induction of differentiated CSSCs, and/or the resulting cells, may be used to treat cell, tissue, or organ damage in a patient by administering to said patient a therapeutically effective amount of a miRNA of interest, or of differentiated CSSCs induced by such miRNAs.

Embodiments comprise the generation of exosomes comprising selected constellations of miRNA species and, as the miRNA can be endogenous to the producing cell, they comprise a versatile method of miRNA delivery. For example, whereas many nucleotide delivery vehicles such as liposomes or nanoparticles require preloading or binding the vehicle with the nucleotide, certain embodiments use the producer cells to create the miRNA and to load the exosome. In this context, embodiments of the invention include can utilize different types vehicles known in the art to deliver polynucleotide cargos (e.g. selected constellations of miRNA species such as those shown in table 1) to cells such as corneal cells (e.g. in an individual suffering from corneal scarring). For example, as discussed throughout this application, typical embodiments of the invention utilize exosomes to deliver polynucleotide cargos into cells. In certain embodiments of the invention, the exosomes are those produced by the CSSC lines disclosed herein. Other embodiments of the invention use different delivery vehicles such as liposomes or nanoparticles to deliver exosome active agents such as polynucleotides into cells (see e.g., U.S. Patent Publication Nos. 20070042979, 20130189351, 20140141070 and 20140112979, the content of which are incorporated herein by reference). Other embodiments of the invention include methods which use viral vectors (e.g. adenovirus, adeno associated virus and the like) to deliver to deliver polynucleotide cargos into cells (see e.g., U.S. Patent Publication Nos. 20040161848, 20100008977 and 20180369418, the content of which are incorporated herein by reference).

The exosome may be used as a substitute for an CSSC or CSSC-CM, as described above. In particular, the exosome may be used for any of the therapeutic purposes that CSSCs or CSSC-CMs are currently being used, or in the future may be used. It will be evident that the methods and compositions described here enable the production of exosomes from corneal stromal stem cells. Thus, any uses of corneal stromal stem cells will equally attach to exosomes from corneal stromal stem cells.

Corneal stromal stem cells as well as the other stem cells having the properties disclosed herein (see, e.g. FIG. 5) and differentiated cells produced by the methods and compositions described here may be used for, or for the preparation of a pharmaceutical composition for, the treatment of a disease. Accordingly, exosomes from these cells (e.g. CSSCs) may be used to treat such diseases. Exosomes from stem cells such as those made according to the methods and compositions described here may be used for a variety of commercially important research, diagnostic, and therapeutic purposes.

Figure 4:
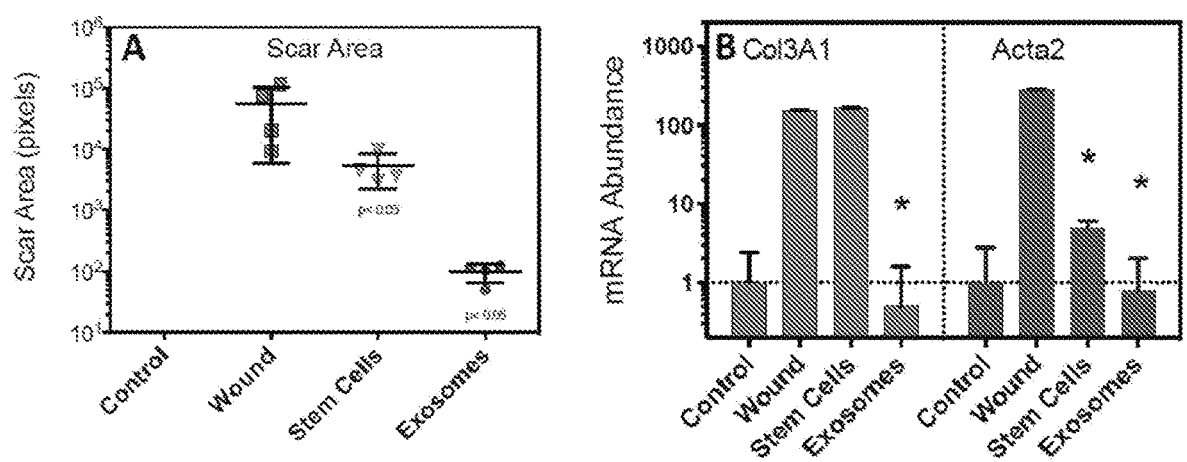
FIGS. 4A and 4B provide graphed data showing how exosomes prevent corneal scarring in a mouse model. Exosomes derived from CSSCs have the to reduce scar size in a mouse corneal wound model (FIG. 4A).

As noted herein, exosome-derived from human CSSCs and certain other stem cells (see, e.g. FIG. 5) have the potential to reduce the scar in a mouse model of corneal wounding. In one illustrative embodiment of the invention, conditioned medium from CSSC was collected after 48 hours' incubation. Medium includes 2% of human serum deprived of exosomes (ultracentrifuged, 2 hours at 50.000 rpm). Isolation of the exosomes included first a concentration of protein (>100 kDa) from the collected conditioned medium), then a polymer-based precipitation of the exosomes and a final step of exosome concentration with a 2-hour ultracentrifugation. As shown in the data presented in FIG. 4, these exosomes showed a similar potential for wound repair as the cells on mice. In view of this, exosomes from CSSCs described here may be used to treat diseases which these functions may have a role in, or whose repair or treatment involves any one or more of these biological processes. Similarly, the exosomes expressed by the CSSCs, singly or in combination, preferably in the form of exosomes (or active components derived therefrom such as those shown in Tables 1 and 2) as described here, may be used to supplement the activity of, or in place of, the CSSCs, or media conditioned by the CSSCs, for the purpose of for example treating or preventing diseases such as corneal scarring.

Typically these methods are practiced on corneal cells present in an individual having corneal scarring. These methods comprise contacting a pharmaceutical composition as disclosed herein with the corneal tissue so that the exosomes (and/or active exosome components) are internalized into cells of the tissue, thereby delivering the polynucleotides into the corneal tissue cells. Typically in these methods, the compositions comprise a plurality of polynucleotides in Table 1; and/or a plurality of expression products of the genes shown in Table 2 (e.g. at least 10, 20 or all of the polynucleotides in Table 1; and at least 10, 20 or a plurality of expression products of the genes shown in Table 2). In some embodiments of these methods, the composition is delivered by direct injection into the corneal stroma. In other embodiments of these methods, the composition is delivered by coating an exosome containing hydrogel in the inner surface of a contact lens and contacting an eye with the contact lens. Such methods can employ a number of reagents and/or method steps that are performed in treatment of corneal scarring (see, e.g. Hertsberg et al., PLoS One. 2017 Mar. 3; 12(3), Basu et al., Sci Transl Med. 2014 Dec. 10; 6(266):266ra172 and Shojaati et al., Regenerative Potential of Stem Cell Derived Exosomes, ARVO annual meeting abstracts program number 3373).

All publications mentioned herein are incorporated herein by reference to disclose and describe the methods and/or materials in connection with which the publications are cited (e.g. U.S. Patent Publication 20170189449, 20170121685, 20170247708 and 20180010133, and Hertsberg et al., PLoS One. 2017 Mar. 3; 12(3), Basu et al., Sci Transl Med. 2014 Dec. 10; 6(266); and Shojaati et al., Regenerative Potential of Stem Cell Derived Exosomes, ARVO annual meeting abstracts program number 3373). Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

TABLE 1

Active Agents Present In Exosomes
That Function To Reduce Corneal Scarring hsa-m1R-107
AACCCGUAGAUCCGAACUUGUG (SEQ ID NO: 1)

hsa-m1R-1197
AGCAGCAUUGUACAGGGCUAUCA (SEQ ID NO: 2)

hsa-m1R-1261
UAGGACACAUGGIJCIJACUUCU (SEQ ID NO: 3)

hsa-miR-1286
AGUGAAUGAUGGGUUCUGACC (SEQ ID NO: 4)

hsa-miR-155-5p
AUGGAUAAGGCUUUGGCLEU (SEQ ID NO: 5)

hsa-miR-212-3p
UGCAGGACCAAGAUGAGCCCU (SEQ ID NO: 6)

hsa-miR-224-5p
UGGAUUUUUGGAUCAGGGA (SEQ ID NO: 7)

hsa-miR-381-5p
UUAGGCCGCAGAUCUGGGUGA (SEQ ID NO: 8)

hsa-miR-411-5p
UUCAAGUAAUUCAGGUG (SEQ ID NO: 9)

hsa-miR-543
UUAAUGCUAAUCGUGAUAGGGGUU (SEQ ID NO: 10)

hsa-miR-548ah-5p
UAGGUAGUUUCAUGUUGUUGGG (SEQ ID NO: 11)

hsa-miR-556-5p
UAACAGUCUCCAGUCACGGCC (SEQ ID NO: 12)

hsa-miR-587
CAGUGCAAUGAUAUUGUCAAAGC (SEQ ID NO: 13)

hsa-miR-612
AAAGCUGGGUUGAGAAGG (SEQ ID NO: 14)

hsa-miR-613
AAUUGCACGGUAUCCAUCUGUA (SEQ ID NO: 15)

hsa-miR-626
GCCUGCUGGGGUGGAACCUGGU (SEQ ID NO: 16)

hsa-miR-888-5p
AUCAUAGAGGAAAAUCCACGU (SEQ ID NO: 17)

hsa-miR-1257
ACUGGACUUGGAGCCAGAAG (SEQ ID NO: 18)

hsa-miR-1290
ACUGGACUUGGUGUCAGAUGG (SEQ ID NO: 19)

hsa-miR-1295a
UGGUAGACUAUGGAACGUAGG (SEQ ID NO: 20)

hsa-miR-1297
AGCGAGGUUGCCCUUUGUAUAU (SEQ ID NO: 21)

hsa-miR-320e
UAGUAGACCGUAUAGCGUACG (SEQ ID NO: 22)

TABLE 1-continued

Active Agents Present In Exosomes
That Function To Reduce Corneal Scarring hsa-miR-363-3p
AGGGUGUGUGUGUUUUU (SEQ ID NO: 23)

hsa-miR-370-3p
AUGGAGAAGGCUUCUGA (SEQ ID NO: 24)

hsa-miR-378f
AAACAAACAUGGUGCACUUCUU (SEQ ID NO: 25)

hsa-miR-378h
UUUCAAGCCAGGGGGCGUUUUUC (SEQ ID NO: 26)

hsa-miR-4455
AAUGCACCUGGGCAAGGAUUCA (SEQ ID NO: 27)

hsa-miR-4531
UUCUCAAGAGGGAGGCAAUCAU (SEQ ID NO: 28)

hsa-miR-498
AAAGUGCUUCCUUUUAGAGGGU (SEQ ID NO: 29)

hsa-miR-502-3p
AAACAUUCGCGGUGCACUUCUU (SEQ ID NO: 30 hsa-miR-514b-5p
AAAAGUGAUUGCAGUGUUUG (SEQ ID NO: 31)

hsa-miR-520c-3p
AAAACUGUAAUUACUUUUGUAC (SEQ ID NO: 32)

hsa-miR-548g-3p
GCUGGUGCAAAAGUAAUGGCCGG (SEQ ID NO: 33)

hsa-miR-548q
UGACAACUAUGGAUGAGCUCU (SEQ ID NO: 34)

hsa-miR-549a
GAUGAGCUCAUUGUAAUAUGAG (SEQ ID NO: 35)

hsa-miR-585-3p
UGGGCGUAUCUGUAUGCUA (SEQ ID NO: 36)

hsa-miR-598-3p
UUUCCAUAGGUGAUGAGUCAC (SEQ ID NO: 37)

hsa-miR-630
UACGUCAUCGUUGUCAUCGUCA (SEQ ID NO: 38)

hsa-miR-644a
GCUGGGCAGGGCUUCUGAGCUCCUU (SEQ ID NO: 39)

hsa-miR-6721-5p
AGGAAUGUUCCUUCUUUGCC (SEQ ID NO: 40)

hsa-miR-761
AGCUGUCUGAAAAUGUCUU (SEQ ID NO: 41)

hsa-miR-769-5p
AGUAUUCUGUACCAGGGAAGGU (SEQ ID NO: 42)

hsa-miR-891b
AGUGUGGCUUUCUUAGAGC (SEQ ID NO: 43)

hsa-miR-100-5p
UGGGCAGGGGCUUAUUGUAGGAG (SEQ ID NO: 44)

hsa-miR-196a-5p
GCAGCAGGGUGAAACUGACACA (SEQ ID NO: 45)

hsa-miR-376a-3p
UGAGACCUCUGGGUUCUGAGCU (SEQ ID NO: 46)

hsa-miR-379-5p
UACUCAAAAAGCUGUCAGUCA (SEQ ID NO: 47)

TABLE 1-continued

Active Agents Present In Exosomes
That Function To Reduce Corneal Scarring hsa-mIR-495-3p
UGCAACUUACCUGAGUCAUUGA (SEQ ID NO: 48)

HSA-MIR-431-5P
UGUCUUGCAGGCCGUCAUGCA (SEQ ID NO: 49)

HSA-MIR-889-3P
UUAAUAUCGGACAACCAUUGU (SEQ ID NO: 50)

HSA-MIR-493-5P
UUGUACAUGGUAGGCUUUCAUU (SEQ ID NO: 51)

HSA-MIR-485-3P
GUCAUACACGGCUCUCCUCUCU (SEQ ID NO: 52)

HSA-MIR-409-3P
GAAUGUUGCUCGGUGAACCCCU (SEQ ID NO: 53)

HSA-MIR-381-3P
UAUACAAGGGCAAGCUCUCUGU (SEQ m NO: 54)

HSA-MIR-493-3P
UGAAGGUCUACUGUGUGCCAGG (SEQ ID NO: 55)

HSA-MIR-4301
UCCCACUACUUCACUUGUGA (SEQ ID NO: 56)

HSA-MIR-654-3P
UAUGUCUGCUGACCAUCACCUU (SEQ ID NO: 57)

HSA-MIR-143-3P
UGAGAUGAAGCACUGUAGCUC (SEQ ID NO: 58)

HSA-MIR-145-5P
GUCCAGUUUUCCCAGGAAUCCCU (SEQ ID NO: 59)

HSA-MIR-323A-3P
CACAUUACACGGUCGACCUCU (SEQ ID NO: 60)

HSA-MIR-4492
GGGGCUGGGCGCGCC (SEQ ID NO: 61)

HSA-MIR-539-3P
AUCAUACAAGGACAAUUUCUUU (SEQ ID NO: 62)

HSA-MIR-665
ACCAGGAGGCUGAGGCCCCU (SEQ ID NO: 63)

HSA-MIR-138-5P
AGCUGGUGUUGUGAAUCAGGCCG (SEQ ID NO: 64)

HSA-MIR-574-3P
CACGCUCAUGCACACACCCACA (SEQ ID NO: 65)

HSA-MIR-1306-5P
CCACCUCCCCUGCAAACGUCCA (SEQ ID NO: 66)

HSA-MIR-92B-3P
UAUUGCACUCGUCCCGGCCUCC (SEQ ID NO: 67)

HSA-MIR.-199A-1//HSA-MIR-199A-2//HSA-MIR-199B
ACAGUAGUCUGCACAUUGGUUA (SEQ ID NO: 68)

HSA-MIR-92A-1//HSA-MIR-92A-2
UAUUGCACUUGUCCCGGCCUGU (SEQ ID NO: 69)

HSA-MIR-29A
UAGCACCAUCUGAAAUCGGUUA (SEQ ID NO: 70)

HSA-MIR-21
UAGCUUAUCAGACUGAUGUUGA (SEQ ID NO: 71)

HSA-MIR-100
AACCCGUAGAUCCGAACUUGUG (SEQ ID NO: 72)

TABLE 1-continued

Active Agents Present In Exosomes
That Function To Reduce Corneal Scarring

HSA-MIR-16-1//HSA-MIR-16-2
UAGCAGCACGUAAAUAUUGGCG (SEQ ID NO: 73)

HSA-MIR-125B-1//HSA-MIR-125B-2
UCCCUGAGACCCUAACUUGUGA (SEQ ID NO: 74)

HSA-MIR-221
AGCUACAUUGUCUGCUGGGUUUC (SEQ ID NO: 75)

HSA-MIR-1246
AAUGGAUUUUUGGAGCAGG (SEQ ID NO: 76)

HSA-MIR-25
CAUUGCACUUGUCUCGGUCUGA (SEQ ID NO: 77)

HSA-MIR-423
UGAGGGGCAGAGAGCGAGACUUU (SEQ ID NO: 78)

HSA-MIR-27B
UUCACAGUGGCUAAGUUCUGC (SEQ ID NO: 79)

HSA-MIR-151A
CUAGACUGAAGCUCCUUGAGG (SEQ ID NO: 80)

HSA-MIR-134
UGUGACUGGUUGACCAGAGGGG (SEQ ID NO: 81)

HSA-MIR-146A
UGAGAACUGAAUUCCAUGGGUU (SEQ ID NO: 82)

HSA-MIR-146B
UGAGAACUGAAUUCCAIUAGGC (SEQ ID NO: 83)

HSA-MIR-191
CAACGGAAUCCCAAAAGCAGCUG (SEQ ID NO: 84)

HSA-MIR-532
CAUGCCUUGAGUGUAGGACCGU (SEQ ID NO: 85)

HSA-MIR-125A
UCCCUGAGACCCUUUAACCUGUGA (SEQ ID NO: 86)

HSA-MIR-409-5P
AGGUUACCCGAGCAACUUUGCAU (SEQ ID NO: 87)

HSA-MIR-222-3P
CUCAGUAGCCAGUGUAGAUCCU (SEQ ID NO: 88)

HSA-MIR-141-3P
UAACACUGUCUGGUAAAGAUGG (SEQ ID NO: 89)

HSA-MIR-590-3P
GAGCUUAUUCAUAAAAGUGCAG (SEQ ID NO: 90)

HSA-MIR-206
UGGAAUGUAAGGAAGUGUGUGG (SEQ ID NO: 91)

HSA-MIR-200C-3P
CGUCUUACCCAGCAGUGUUUGG (SEQ ID NO: 92)

HSA-MIR-208A-3P
GAGCUUUUGGCCCGGGUUAUAC (SEQ ID NO: 93)

HSA-MIR-133A-3P
UUUGGUCCCCUUCAACCAGCUG (SEQ ID NO: 94)

HSA-LET-7I
UGAGGUAGUAGUUUGUGCUGUU (SEQ ID NO: 95)

HSA-LET-7B
UGAGGUAGUAGGUUGUGUGGUU (SEQ ID NO: 96)

HSA-PIR-23210
CCTCTGTCTGCCTTAACGTCTTCCTGAATC (SEQ ID NO: 97)

TABLE 1-continued

Active Agents Present In Exosomes
That Function To Reduce Corneal Scarring

PIR-HSA-32195
ATGCAGTGTGGAACACAATGAACTGAA (SEQ ID NO: 98)

PIR-HSA-32161
CCCCCCACTGCTAAATTTGACTGGC (SEQ ID NO: 99)

PIR-HSA-32162
CACAATGCTGACACTCAAACTGCTGACA (SEQ ID NO: 100)

PIR-HSA-32159
CCCCCACTGCTAAATTTGACTGG (SEQ ID NO: 101)

PIR-HSA-23209
CCTCTGTCGCTGATGTTTCTTAAGAGTGAGC (SEQ ID NO: 102)

TRNA-LYS-CTT-CHR16-1
GCCCAGCUAGCUCAGUCGGUAGAGCAUGAGACUCUUAAUCUCAGGGUCAU
GGGUUUGAGCCCCACGUUUGGUG (SEQ ID NO: 103)

ENST00000567527.I_RP11-701H24.4
TGGATCGATGATGACTTCCATATATACATTCCTTGGAAAGCTGAACAAAA
TGAGTGAAAACTCTATACTGTCATCCTCGTCGAACTGAGGTCCAGCACAT
TACTCCAACAGGGGCTAGACAGAGAAGGCCAACATCCGTTTGTTGACATG
GGTTATATCAAGGCGTCTGTTCAGGCTTAGAATGTGGTCTCTTATGGGTG
ATGGGGGTCACAGGAGAGTGGTGGCTCCCATGTATAGGAAATTTCTTGTT
TGAAGGACTGTCAGTGAGGGTGGGTAACACATGCATTGTCTGCAGGACTA
GGTGAATGTCCATGTGGCCTAGCAAGAGTTAGCTGGTAGCCCGCCTCTGG
TTGCCAATTTGTTCTTGAGTCCTTGTTCTGGGTTCTCAGGTCCCACGGAG
GAAAACAGATCTGTGTGGTTGAGAGGTGGGTACAAGGCCGCATCTTTGTC
ATTTGTTGGCTAACTTTGTCCTTGGTTGAGGACATTAGAGTTTTGGTCAC
CAGGCATAGCCTATGTGCCTTTGTGCCCGTGTTGTATCCCACGTGTTTTG
AGGACATGTATTTTGCACGTAAAGGTGAGCTCCTGCTCCAAGCTGGTTCT
GATACCAAAGGAGTCCCTGGCTTATCCTAAACTCATGGTAGGTTAAAGCC
TTCCTCCTTAGGGGTTCAGGGCCGCAAGGCTTTTGTGAGTGGCATTGCAG
GCGTTGAAGCAGTGATGTTGAGAGGGATGGTCAATGTCAGTGCTCTTTAG
CAGGATGGTGTACTGCAGGGGCCCCAGCCCCGAGACGAGCATCCCTGCA
TCCATGCATTTCTGCCTCCATGAACAGGGGAGGCCAGAGACAGGCAGATA
GTAGATAAATTGCAGGGGACTGGATGACATGGCCCTCGTGACCTGTGCAC
CTGTCTGTCTTTCTGAAGCACGCCTGTGTTAACTCTGCACCTCCCAGGTA
GCACTGGCATGGAGGGCAGGCACATGTTGGTGAGGGACAATTGTTACCTT
GTGTGAGCTGCGGAGATACCAGGAAGCCCCTGGACACAAATGGCAAAGGC
TCCTTCGGAAGTTGTTGGATCCCTTCTGAATGTAAGCACTTCTTTCCCAG
AGCACTCTGAGTTTCCTCATTTGCAGGGACAAATACTGTGCGTGGATCGA
TGATGACTTCCACATATACATTCCTTGGAAAGCTGAACAAAATGAGTGAA
AACTCTATACCGTCATCCTCGTCGAACTGAGGTCCA (SEQ ID NO: 104)

TABLE 1-continued

Active Agents Present In Exosomes
That Function To Reduce Corneal Scarring

ENST00000363762.1_SNORD113-7
TGGATCAATGATGAGTATGCGTGGGGCATCTGAATCAAATATTCTGATTA
TACCCTGTCTGTATCTCTGAGGTCCA (SEQ ID NO: 105)

ENST00000365080.1_SNORD113-9
TGGATCAATGATGAGTACCCTGGGGTGTCTGAATCTTGGATTTTGATTAA
ACCCTATAACTCTGAGGTCCA (SEQ ID NO: 106)

ENST00000385300.1_CARMN
GCGCAGCGCCCTGTCTCCCAGCCTGAGGTGCAGTGCTGCATCTCTGGTCA
GTTGGGAGTCTGAGATGAAGCACTGTAGCTCAGGAAGAGAGAAGTTGTTC
TGCAGC ( SEQ ID NO: 107)

Table 2: Gene Expression Products that Function to Reduce Corneal Scarring

Table 2 provides a list of genes whose expression products (typically a protein or a polynucleotide) are present in exosomes shown have an ability to reduce corneal scarring. As shown by the Ensemble Gene ID designations in this list (e.g. "ENSG00000106244"), these are well defined and cataloged genes whose sequences are found in the Human Protein Atlas. In particular, Ensembl is a genome browser for vertebrate genomes that supports research in comparative genomics, evolution, sequence variation and transcriptional regulation. Stable identifiers are ways that databases, such as Ensembl, can label the features, such as genes, transcripts, exons or proteins, in their database. The identifiers aim to be unambiguous and consistent across Ensembl releases. An Ensembl stable ID consists of five parts: ENS (species)(object type)(identifier). The first part, 'ENS', tells you that it's an Ensembl ID. The second part is a three-letter species code. For human, there is no species code so IDs are in the form ENS(object type)(identifier). The third part is a one- or two-letter object type. For example E for exon, FM for protein family, G for gene, GT for gene tree, P for protein, R for regulatory feature and T for transcript. The identifier is the number to that object. Combinations of prefixes and identifiers are unique. Using the Ensembl nomenclature, for example, ENSG00000196154 is shown to be S100 calcium binding protein A4, while ENSG00000129824 is shown to be ribosomal protein S4 etc. etc.

TABLE 2

ENSG00000067048, ENSG00000144895, ENSG00000122497, ENSG00000156298,
ENSG00000133818, ENSG00000146066, ENSG00000141101, ENSG00000010256,
EN5G00000105583, ENSG00000152082, ENSG00000151366, ENSG00000225746,
ENSG00000185561, ENSG00000165264, ENSG00000200487, ENSG00000185201,
ENSG00000182512, ENSG00000091483, ENSG00000137547, ENSG00000264229,
ENSG00000197409, ENSG00000176105, ENSG00000128050, ENSG00000125249,
ENSG00000110104, ENSG00000196507, ENSG00000266467, ENSG00000197894,
ENSG00000245910, ENSG00000164172, ENSG00000119865, ENSG00000162576,
ENSG00000148303, ENSG00000163386, ENSG00000198356, ENSG00000147164,
ENSG00000176046, ENSG00000122566, ENSG00000122033, ENSG00000168028,
ENSG00000164032, ENSG00000096746, ENSG00000173530, ENSG00000164022,
ENSG00000183648, ENSG00000175764, ENSG00000152484, ENSG00000265813,
ENSG00000198961, ENSG00000141522, ENSG00000135069, ENSG00000188229,
ENSG00000173915, ENSG00000169021, ENSG00000183684, ENSG00000174547,
ENSG00000174780, ENSG00000147955, ENSG00000240869, ENSG00000239672,
ENSG00000130741, ENSG00000101367, ENSG00000213523, ENSG00000178952,
ENSG00000108179, ENSG00000135316, ENSG00000183617, ENSG00000143727,
ENSG00000241529, ENSG00000109113, ENSG00000138430, ENSG00000136732,
ENSG00000158526, ENSG00000102699, ENSG00000115415, ENSG00000143543, and
ENSG00000106244.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A pharmaceutical composition comprising:
 a plurality of polynucleotides comprising SEQ ID NO: 1-SEQ ID NO: 107; and
 a pharmaceutical excipient selected from the group consisting of:
 a preservative, a tonicity adjusting agent, a detergent, a viscosity adjusting agent, a sugar or a pH adjusting agent.

2. The pharmaceutical composition of claim 1, wherein the polynucleotides are disposed within one or more exosomes.

3. The pharmaceutical composition of claim 2, further comprising a hydrogel in which the exosomes are disposed.

4. The pharmaceutical composition of claim 2, wherein the exosomes are produced by:
 corneal stromal stem cells (CSSC);
 adipose derived stem cells (ADSC);
 umbilical cord stem cells (UMSC); or
 bone marrow derived stem cells (BDMSC).

5. The pharmaceutical composition of claim 2, wherein the exosomes are present in the composition in amounts sufficient to treat a patient diagnosed with epithelial defects, persistent sterile corneal ulcers, neurotrophic corneal ulcers, keratoconus, and corneal scarring due to bacterial or viral keratitis.

6. The pharmaceutical composition of claim 2, wherein the exosomes are produced by an immortalized cell line.

7. The pharmaceutical composition of claim 1, wherein:
 the composition comprises an excipient used in compositions formulated for direct injection into the corneal stroma; and/or
 the composition coats a contact lens.

* * * * *